(12) United States Patent
Weckwerth et al.

(10) Patent No.: US 8,777,935 B2
(45) Date of Patent: *Jul. 15, 2014

(54) OPTICAL SENSOR AND METHOD FOR IDENTIFYING THE PRESENCE OF SKIN

(75) Inventors: Mark V. Weckwerth, Pleasanton, CA (US); Tobin C. Island, Oakland, CA (US); Robert E. Grove, Pleasanton, CA (US)

(73) Assignee: Tria Beauty, Inc., Pleasanton, CA (US)

( * ) Notice: Subject to any disclaimer, the term of this patent is extended or adjusted under 35 U.S.C. 154(b) by 1159 days.

This patent is subject to a terminal disclaimer.

(21) Appl. No.: 12/193,544

(22) Filed: Aug. 18, 2008

(65) Prior Publication Data

US 2009/0125006 A1   May 14, 2009

Related U.S. Application Data

(63) Continuation-in-part of application No. 10/787,720, filed on Feb. 25, 2004, now Pat. No. 7,413,567.

(51) Int. Cl.
*A61B 18/18* (2006.01)

(52) U.S. Cl.
USPC .............. 606/9; 606/10; 606/12; 606/13

(58) Field of Classification Search
CPC .............. A61B 18/203; A61B 2018/00452; A61B 2018/00476
USPC ................................. 606/10, 9
See application file for complete search history.

(56) References Cited

U.S. PATENT DOCUMENTS

| | | | |
|---|---|---|---|
| 3,307,533 A | 3/1967 | Meredith et al. | 601/150 |
| 3,538,919 A | 11/1970 | Meyer | 606/36 |
| 3,622,743 A | 11/1971 | Muncheryan | 219/121.63 |
| 3,693,623 A | 9/1972 | Harte et al. | 606/9 |
| 3,821,510 A | 6/1974 | Muncheryan | 219/121.79 |
| 3,834,391 A | 9/1974 | Block | 128/303.1 |
| 4,140,130 A | 2/1979 | Storm, III | 607/154 |

(Continued)

FOREIGN PATENT DOCUMENTS

| | | | | |
|---|---|---|---|---|
| CN | 2442726 Y | 8/2001 | | A63H 33/00 |
| DE | 19629978 A1 | 1/1998 | | F41A 33/02 |

(Continued)

OTHER PUBLICATIONS

European Office Action, European application No. 04 714 604.8, 5 pages, Nov. 16, 2010.

(Continued)

*Primary Examiner* — Bill Thomson
*Assistant Examiner* — John R Downey
(74) *Attorney, Agent, or Firm* — King & Spalding L.L.P.

(57) ABSTRACT

A sensor for detecting the presence of skin is disclosed, one configuration of which uses multiple light emitting diodes, each of a unique wavelength band, and a broad-band photodetector to measure the remission of light at multiple wavelengths from a material being analyzed. Characteristics of the spectral remission of the material are used to discriminate human skin from materials that are not human skin. Further, an aesthetic medical device utilizing such a sensor in which the device is inhibited from operation if skin has not been detected. The incorporation of a skin sensor improves the safety of devices that emit radiation that otherwise would pose a hazard if not directed onto skin.

20 Claims, 6 Drawing Sheets

(56) References Cited

U.S. PATENT DOCUMENTS

| | | | |
|---|---|---|---|
| 4,232,678 A | 11/1980 | Skovajsa | 607/89 |
| 4,240,738 A | 12/1980 | Praamsma | |
| 4,354,092 A | 10/1982 | Manabe et al. | 219/225 |
| 4,388,924 A | 6/1983 | Weissman et al. | 606/9 |
| 4,423,736 A | 1/1984 | DeWitt et al. | 128/633 |
| 4,449,528 A | 5/1984 | Auth et al. | 606/31 |
| 4,551,628 A | 11/1985 | Grossman | 250/503.1 |
| 4,573,466 A | 3/1986 | Simada et al. | 606/11 |
| 4,592,353 A | 6/1986 | Daikuzono | 606/16 |
| 4,608,978 A | 9/1986 | Rohr | 606/9 |
| 4,617,926 A | 10/1986 | Sutton | 606/9 |
| 4,690,141 A | 9/1987 | Castel et al. | 607/90 |
| 4,733,660 A | 3/1988 | Itzkan | 606/9 |
| 4,829,262 A | 5/1989 | Furumoto | 359/346 |
| 4,846,184 A | 7/1989 | Comment et al. | 128/633 |
| 4,860,744 A | 8/1989 | Johnson et al. | 128/303.1 |
| 4,905,690 A | 3/1990 | Ohshiro et al. | 607/89 |
| 4,930,504 A | 6/1990 | Diamantopoulos et al. | 607/88 |
| 5,057,104 A | 10/1991 | Chess | 606/9 |
| 5,059,013 A | 10/1991 | Jain | 359/503 |
| 5,059,192 A | 10/1991 | Zaias | 606/9 |
| 5,071,417 A | 12/1991 | Sinofsky | 606/8 |
| 5,075,971 A | 12/1991 | Mccambridge | 30/133 |
| 5,107,832 A | 4/1992 | Guibert et al. | 607/96 |
| 5,109,465 A | 4/1992 | Klopotek | 385/133 |
| 5,226,907 A | 7/1993 | Tankovich | 606/133 |
| 5,233,337 A | 8/1993 | Takahashi | 345/82 |
| 5,259,380 A | 11/1993 | Mendes et al. | 607/115 |
| 5,282,797 A | 2/1994 | Chess | 606/9 |
| 5,295,052 A | 3/1994 | Chin et al. | |
| 5,344,418 A | 9/1994 | Ghaffari | 606/9 |
| 5,360,426 A | 11/1994 | Muller et al. | 606/13 |
| 5,401,270 A | 3/1995 | Muller et al. | 606/13 |
| 5,405,368 A | 4/1995 | Eckhouse | 607/88 |
| 5,425,728 A | 6/1995 | Tankovich | 606/9 |
| 5,431,647 A | 7/1995 | Purcell, Jr. et al. | 606/16 |
| 5,464,434 A | 11/1995 | Alt | 607/6 |
| 5,464,436 A | 11/1995 | Smith | 607/89 |
| 5,473,408 A | 12/1995 | Hoffman et al. | 355/53 |
| 5,481,385 A | 1/1996 | Zimmerman et al. | 349/62 |
| 5,486,172 A | 1/1996 | Chess | 606/20 |
| 5,519,534 A | 5/1996 | Smith et al. | 359/599 |
| 5,549,660 A | 8/1996 | Mendes et al. | 607/88 |
| 5,556,612 A | 9/1996 | Anderson et al. | 424/59 |
| 5,578,022 A | 11/1996 | Scherson et al. | 604/304 |
| 5,595,568 A | 1/1997 | Anderson et al. | 606/9 |
| 5,606,798 A | 3/1997 | Kelman | 30/41.5 |
| 5,611,798 A | 3/1997 | Eggers | 606/31 |
| 5,624,435 A | 4/1997 | Furumoto et al. | 606/10 |
| 5,628,744 A * | 5/1997 | Coleman et al. | 606/12 |
| 5,630,811 A | 5/1997 | Miller | 606/9 |
| 5,632,741 A | 5/1997 | Zavislan et al. | 606/9 |
| 5,643,252 A | 7/1997 | Waner et al. | 606/9 |
| 5,647,866 A | 7/1997 | Zaiase et al. | 606/9 |
| 5,658,323 A | 8/1997 | Miller | 607/89 |
| 5,662,643 A | 9/1997 | Kung et al. | 606/3 |
| 5,669,916 A | 9/1997 | Anderson | 606/133 |
| 5,683,380 A | 11/1997 | Eckhouse et al. | 606/9 |
| 5,700,240 A | 12/1997 | Barwick, Jr. et al. | 604/22 |
| 5,707,403 A | 1/1998 | Grove et al. | 607/89 |
| 5,728,090 A | 3/1998 | Martin et al. | 606/3 |
| 5,735,844 A | 4/1998 | Anderson et al. | 606/9 |
| 5,743,901 A | 4/1998 | Grove et al. | 606/9 |
| 5,752,948 A | 5/1998 | Tankovich et al. | 606/9 |
| 5,752,949 A | 5/1998 | Tankovich et al. | 606/9 |
| 5,766,214 A | 6/1998 | Mehl, Sr. et al. | 606/9 |
| 5,769,844 A | 6/1998 | Ghaffari | 606/16 |
| 5,792,137 A | 8/1998 | Carr et al. | 606/29 |
| 5,814,040 A | 9/1998 | Nelson et al. | 606/9 |
| 5,817,089 A | 10/1998 | Tankovich et al. | 606/9 |
| 5,820,625 A | 10/1998 | Izawa et al. | 606/9 |
| 5,824,023 A | 10/1998 | Anderson | 607/88 |
| 5,830,208 A | 11/1998 | Muller | 606/9 |
| 5,843,072 A | 12/1998 | Furumoto et al. | 606/9 |
| 5,846,252 A | 12/1998 | Mehl, Sr. | 606/133 |
| 5,849,029 A * | 12/1998 | Eckhouse et al. | 607/104 |
| 5,853,407 A | 12/1998 | Miller | 606/9 |
| 5,868,732 A | 2/1999 | Waldman et al. | 606/9 |
| 5,871,479 A | 2/1999 | Furumoto et al. | 606/9 |
| 5,871,480 A | 2/1999 | Tankovich | 606/9 |
| 5,871,521 A | 2/1999 | Kaneda et al. | 607/89 |
| 5,879,346 A | 3/1999 | Waldman et al. | 606/9 |
| 5,885,273 A | 3/1999 | Eckhouse et al. | 606/9 |
| 5,944,748 A | 8/1999 | Mager et al. | 607/88 |
| 5,966,210 A | 10/1999 | Rosow et al. | 356/213 |
| 5,968,034 A | 10/1999 | Fullmer et al. | 606/9 |
| 5,989,267 A | 11/1999 | Anderson | 606/133 |
| 6,015,404 A | 1/2000 | Altshuler et al. | 606/9 |
| RE36,634 E | 3/2000 | Ghaffari | 606/9 |
| 6,059,765 A | 5/2000 | Cole et al. | 604/500 |
| 6,072,551 A | 6/2000 | Jannson et al. | 349/64 |
| 6,080,146 A | 6/2000 | Altshuler et al. | 606/9 |
| 6,096,029 A | 8/2000 | O'donnell, Jr. | 606/9 |
| 6,104,959 A | 8/2000 | Spertell | 607/101 |
| 6,106,514 A | 8/2000 | O'donnell, Jr. | 606/9 |
| 6,114,862 A | 9/2000 | Tartagni | 324/662 |
| 6,134,475 A | 10/2000 | Will | 607/98 |
| 6,138,041 A | 10/2000 | Yahia | 455/569.2 |
| 6,144,536 A | 11/2000 | Zimmerman et al. | 361/31 |
| 6,160,831 A | 12/2000 | Kleinschmidt et al. | 372/57 |
| 6,168,831 B1 | 1/2001 | Khan et al. | 427/240 |
| 6,171,301 B1 | 1/2001 | Nelson et al. | 606/9 |
| 6,183,500 B1 | 2/2001 | Kohler | 607/88 |
| 6,183,773 B1 | 2/2001 | Anderson | 424/450 |
| 6,188,495 B1 | 2/2001 | Inoue et al. | 398/139 |
| 6,197,020 B1 | 3/2001 | O'donnell, Jr. | 606/9 |
| 6,208,749 B1 | 3/2001 | Gutkowicz-Krusin et al. | 382/128 |
| 6,214,034 B1 | 4/2001 | Azar | 607/89 |
| 6,228,074 B1 | 5/2001 | Almeida | 606/9 |
| 6,251,127 B1 | 6/2001 | Biel | 607/88 |
| 6,264,649 B1 | 7/2001 | Whitcroft et al. | 606/22 |
| 6,269,818 B1 | 8/2001 | Lui et al. | 128/898 |
| 6,273,884 B1 | 8/2001 | Altshuler et al. | 606/9 |
| 6,273,885 B1 | 8/2001 | Koop et al. | 606/9 |
| 6,277,111 B1 | 8/2001 | Clement et al. | 606/9 |
| 6,280,438 B1 | 8/2001 | Eckhouse et al. | 606/9 |
| 6,290,713 B1 | 9/2001 | Russell | 607/88 |
| 6,306,130 B1 | 10/2001 | Anderson et al. | 606/27 |
| 6,322,584 B2 | 11/2001 | Ingle et al. | 607/96 |
| 6,379,376 B1 | 4/2002 | Lubart | 607/88 |
| 6,408,212 B1 | 6/2002 | Neev | 607/100 |
| 6,413,255 B1 | 7/2002 | Stern | 606/41 |
| 6,413,268 B1 | 7/2002 | Hartman | 607/94 |
| 6,428,198 B1 | 8/2002 | Saccomanno et al. | 385/147 |
| 6,436,127 B1 | 8/2002 | Anderson et al. | 607/89 |
| 6,440,122 B1 | 8/2002 | Shimoji | 606/2 |
| 6,441,943 B1 | 8/2002 | Roberts et al. | 359/267 |
| 6,451,007 B1 | 9/2002 | Koop et al. | 606/9 |
| 6,485,484 B1 | 11/2002 | Connors et al. | 606/9 |
| 6,494,900 B1 | 12/2002 | Salansky et al. | 607/89 |
| 6,508,813 B1 * | 1/2003 | Altshuler | 606/9 |
| 6,511,475 B1 | 1/2003 | Altshuler et al. | 606/9 |
| 6,514,242 B1 | 2/2003 | Vasily et al. | 606/9 |
| 6,516,013 B1 | 2/2003 | Patzel et al. | 372/29.02 |
| 6,517,532 B1 | 2/2003 | Altshuler et al. | 606/9 |
| 6,533,775 B1 | 3/2003 | Rizoiu | 606/9 |
| 6,536,914 B2 | 3/2003 | Hoelen et al. | |
| 6,548,781 B1 | 4/2003 | Brunwinkel | 219/121.73 |
| 6,563,853 B2 | 5/2003 | Heist et al. | 372/57 |
| 6,567,696 B2 | 5/2003 | Voznesensky et al. | 607/3 |
| 6,572,637 B1 | 6/2003 | Yamazaki et al. | 607/89 |
| 6,600,951 B1 | 7/2003 | Anderson | 604/20 |
| 6,605,080 B1 | 8/2003 | Altshuler et al. | 606/3 |
| 6,610,052 B2 | 8/2003 | Furumoto | 606/9 |
| 6,621,702 B2 | 9/2003 | Elias et al. | 361/700 |
| 6,637,924 B2 | 10/2003 | Pelka et al. | 362/555 |
| 6,641,044 B2 | 11/2003 | Plesko | 235/462.49 |
| 6,648,904 B2 | 11/2003 | Altshuler et al. | 607/96 |
| 6,653,618 B2 | 11/2003 | Zenzie | 250/221 |
| 6,659,999 B1 | 12/2003 | Anderson et al. | 606/9 |
| 6,660,000 B2 | 12/2003 | Neuberger et al. | 606/9 |
| 6,663,620 B2 | 12/2003 | Altshuler et al. | 606/9 |
| 6,663,659 B2 | 12/2003 | Mcdaniel | 607/88 |

(56) References Cited

U.S. PATENT DOCUMENTS

| | | | |
|---|---|---|---|
| 6,666,856 B2 | 12/2003 | Connors et al. | 606/9 |
| 6,723,090 B2 | 4/2004 | Altshuler et al. | 606/9 |
| 6,749,624 B2 | 6/2004 | Knowlton | 607/104 |
| 6,758,845 B1 | 7/2004 | Weckwerth et al. | 606/9 |
| 6,790,205 B1 | 9/2004 | Yamazaki et al. | 606/9 |
| 6,808,287 B2 | 10/2004 | Lebens et al. | 362/184 |
| 6,817,997 B2 | 11/2004 | Furuno et al. | 606/9 |
| 6,872,221 B2 | 3/2005 | Lytle | 607/89 |
| 6,887,260 B1 | 5/2005 | Mcdaniel | 607/88 |
| 6,902,563 B2 | 6/2005 | Wilkens et al. | 606/9 |
| 6,955,672 B2 | 10/2005 | Cense et al. | 606/9 |
| 6,957,905 B1 | 10/2005 | Pritchard et al. | 362/554 |
| 6,976,984 B2 * | 12/2005 | Cense et al. | 606/9 |
| 7,029,469 B2 | 4/2006 | Vasily et al. | 606/9 |
| 7,068,910 B2 | 6/2006 | Duine et al. | |
| 7,077,544 B2 | 7/2006 | Parker | 607/90 |
| 7,083,610 B1 | 8/2006 | Murray et al. | 606/9 |
| 7,115,123 B2 | 10/2006 | Knowlton et al. | 606/41 |
| 7,118,563 B2 | 10/2006 | Weckwerth et al. | 606/9 |
| 7,204,832 B2 | 4/2007 | Altshuler et al. | 606/9 |
| 7,250,045 B2 | 7/2007 | Island et al. | 606/17 |
| 7,250,047 B2 | 7/2007 | Anderson et al. | 606/32 |
| 7,413,567 B2 | 8/2008 | Weckwerth et al. | 606/10 |
| 7,452,356 B2 | 11/2008 | Grove et al. | 606/9 |
| 7,762,964 B2 | 7/2010 | Slatkine | 601/7 |
| 7,981,111 B2 | 7/2011 | Grove et al. | 606/27 |
| 8,346,347 B2 | 1/2013 | Altshuler et al. | 600/476 |
| 8,551,104 B2 | 10/2013 | Weckwerth et al. | 606/89 |
| 2001/0023363 A1 | 9/2001 | Harth et al. | 607/90 |
| 2001/0046131 A1 | 11/2001 | Hoelen et al. | |
| 2001/0048801 A1 | 12/2001 | Saccomanno et al. | 385/147 |
| 2002/0005475 A1 | 1/2002 | Zenzie | 250/221 |
| 2002/0015430 A1 | 2/2002 | Osmanow et al. | 372/55 |
| 2002/0031160 A1 | 3/2002 | Desor | 372/57 |
| 2002/0049483 A1 | 4/2002 | Knowlton | 607/101 |
| 2002/0091377 A1 | 7/2002 | Anderson et al. | 606/9 |
| 2002/0097587 A1 | 7/2002 | Krietzman et al. | 362/553 |
| 2002/0128635 A1 | 9/2002 | Altshuler et al. | 606/9 |
| 2002/0128695 A1 | 9/2002 | Harth et al. | 607/88 |
| 2002/0151887 A1 | 10/2002 | Stern et al. | 606/41 |
| 2002/0161357 A1 | 10/2002 | Anderson et al. | 606/9 |
| 2002/0161418 A1 | 10/2002 | Wilkens et al. | 607/90 |
| 2002/0173780 A1 | 11/2002 | Altshuler et al. | 606/9 |
| 2002/0173833 A1 | 11/2002 | Korman et al. | 607/88 |
| 2002/0183811 A1 | 12/2002 | Irwin | 607/94 |
| 2003/0004499 A1 | 1/2003 | Mcdaniel | 606/3 |
| 2003/0009158 A1 | 1/2003 | Perricone | 606/9 |
| 2003/0032950 A1 | 2/2003 | Altshuler et al. | 606/9 |
| 2003/0036751 A1 | 2/2003 | Anderson et al. | 606/9 |
| 2003/0046825 A1 | 3/2003 | Slingo | 34/96 |
| 2003/0050561 A1 | 3/2003 | Bazin et al. | 600/476 |
| 2003/0055413 A1 | 3/2003 | Altshuler et al. | 606/9 |
| 2003/0055414 A1 | 3/2003 | Altshuler et al. | 606/9 |
| 2003/0065314 A1 * | 4/2003 | Altshuler et al. | 606/9 |
| 2003/0080755 A1 | 5/2003 | Kobayashi | |
| 2003/0094714 A1 | 5/2003 | Buazza et al. | 264/1.38 |
| 2003/0105069 A1 | 6/2003 | Robinson et al. | 514/185 |
| 2003/0112623 A1 | 6/2003 | Yu et al. | 362/118 |
| 2003/0133292 A1 | 7/2003 | Mueller et al. | 362/231 |
| 2003/0138249 A1 | 7/2003 | Merola et al. | 396/661 |
| 2003/0146122 A1 | 8/2003 | Westfield et al. | 206/349 |
| 2003/0169400 A1 | 9/2003 | Buazza et al. | 351/159.62 |
| 2003/0177657 A1 | 9/2003 | Andis et al. | 34/96 |
| 2003/0195494 A1 | 10/2003 | Altshuler et al. | 606/9 |
| 2003/0199859 A1 | 10/2003 | Altshuler et al. | 606/9 |
| 2003/0216795 A1 | 11/2003 | Harth et al. | 607/88 |
| 2003/0220633 A1 | 11/2003 | Angeley et al. | 606/18 |
| 2003/0232356 A1 | 12/2003 | Dooley et al. | 435/6.12 |
| 2003/0233138 A1 | 12/2003 | Spooner | 607/93 |
| 2004/0006328 A1 | 1/2004 | Anderson | 604/501 |
| 2004/0010298 A1 | 1/2004 | Altshuler et al. | 607/88 |
| 2004/0010299 A1 | 1/2004 | Tolkoff et al. | 607/88 |
| 2004/0034319 A1 | 2/2004 | Anderson et al. | 604/20 |
| 2004/0034341 A1 | 2/2004 | Altshuler et al. | 606/3 |
| 2004/0036975 A1 | 2/2004 | Slatkine | 359/584 |
| 2004/0046108 A1 | 3/2004 | Spector | 250/227.13 |
| 2004/0054386 A1 | 3/2004 | Martin et al. | 607/88 |
| 2004/0073079 A1 | 4/2004 | Altshuler et al. | 600/1 |
| 2004/0093042 A1 | 5/2004 | Altshuler et al. | 607/88 |
| 2004/0116913 A1 | 6/2004 | Pilcher et al. | 606/9 |
| 2004/0120151 A1 | 6/2004 | Ostler et al. | |
| 2004/0122492 A1 | 6/2004 | Harth et al. | 607/88 |
| 2004/0167499 A1 | 8/2004 | Grove et al. | 606/9 |
| 2004/0167500 A1 | 8/2004 | Weckwerth et al. | 606/9 |
| 2004/0167501 A1 | 8/2004 | Island et al. | 606/9 |
| 2004/0167502 A1 | 8/2004 | Weckwerth et al. | 606/9 |
| 2004/0167592 A1 | 8/2004 | Grove et al. | 607/96 |
| 2004/0176754 A1 | 9/2004 | Island et al. | 606/9 |
| 2004/0176823 A1 | 9/2004 | Island et al. | 607/88 |
| 2004/0225339 A1 | 11/2004 | Yaroslavsky et al. | 607/88 |
| 2004/0233655 A1 | 11/2004 | Zimmerman et al. | 362/19 |
| 2004/0252940 A1 | 12/2004 | Atac et al. | 385/31 |
| 2005/0008049 A1 | 1/2005 | Oomori et al. | 372/36 |
| 2005/0038418 A1 | 2/2005 | Altshuler et al. | 606/9 |
| 2005/0069566 A1 | 3/2005 | Tamarkin et al. | 424/401 |
| 2005/0085878 A1 | 4/2005 | Wilkens et al. | 607/94 |
| 2005/0107849 A1 | 5/2005 | Altshuler et al. | 607/88 |
| 2005/0234527 A1 | 10/2005 | Slatkine | 607/89 |
| 2005/0276072 A1 | 12/2005 | Hayashi et al. | |
| 2006/0142750 A1 | 6/2006 | Da Silva et al. | 606/27 |
| 2006/0206103 A1 | 9/2006 | Altshuler et al. | |
| 2007/0025947 A1 | 2/2007 | Hansenne et al. | 424/70.22 |
| 2007/0027440 A1 | 2/2007 | Altshuler et al. | 606/9 |
| 2007/0032847 A1 | 2/2007 | Weckwerth et al. | 607/93 |
| 2007/0060819 A1 * | 3/2007 | Altshuler et al. | 600/475 |
| 2007/0129711 A1 | 6/2007 | Altshuler et al. | |
| 2007/0292461 A1 | 12/2007 | Tamarkin et al. | 424/401 |
| 2008/0027518 A1 * | 1/2008 | Island et al. | 607/88 |
| 2008/0125834 A1 | 5/2008 | Hendrix et al. | 607/88 |
| 2008/0147053 A1 | 6/2008 | Kang et al. | 606/9 |
| 2009/0043294 A1 * | 2/2009 | Island et al. | 606/9 |
| 2009/0270848 A1 * | 10/2009 | Weckwerth et al. | 606/9 |
| 2010/0069898 A1 * | 3/2010 | O'Neil et al. | 606/9 |

FOREIGN PATENT DOCUMENTS

| | | | |
|---|---|---|---|
| DE | 10044662 A1 | 3/2002 | A61K 31/60 |
| DE | 10360503 A1 | 7/2005 | A61K 8/06 |
| EP | 0761257 A2 | 3/1997 | A61B 18/20 |
| EP | 0933096 A2 | 8/1999 | A61B 17/00 |
| EP | 1116476 A2 | 7/2001 | A61B 18/20 |
| EP | 1168535 A1 | 1/2002 | H01S 5/022 |
| EP | 1358872 A1 | 11/2003 | A61K 31/192 |
| FR | 2665366 A1 | 2/1992 | A61N 1/32 |
| FR | 2932679 A1 | 12/2009 | A61K 8/36 |
| JP | 06-273758 A | 9/1994 | G02F 1/1335 |
| JP | 06-334950 A | 12/1994 | H04N 5/74 |
| JP | 11244295 A | 9/1999 | A61B 18/20 |
| JP | 2000300683 A | 10/2000 | A61B 18/20 |
| JP | 2000515410 | 11/2000 | A61B 18/20 |
| JP | 2001252363 A | 9/2001 | A61B 17/00 |
| JP | 2002253573 A | 9/2002 | A61B 18/20 |
| JP | 2003024458 A | 1/2003 | A61N 5/06 |
| JP | 2004136019 A | 5/2004 | A45D 26/00 |
| JP | 2004527330 A | 9/2004 | A61B 17/00 |
| JP | 2006518614 A | 8/2006 | A61B 18/20 |
| JP | 2006525036 A | 11/2006 | A61B 17/00 |
| JP | 2007508243 A | 4/2007 | |
| JP | 2009509140 A | 3/2009 | A61B 5/00 |
| JP | 5146517 B2 | 2/2013 | H01L 21/28 |
| WO | 96/14083 A1 | 5/1996 | A23L 1/015 |
| WO | 00/02491 A1 | 1/2000 | A61K 41/00 |
| WO | 02/094116 A1 | 11/2002 | A61B 18/18 |
| WO | 03/001984 A2 | 1/2003 | |
| WO | 03/017824 A2 | 3/2003 | A61B 18/00 |
| WO | 03/043697 | 5/2003 | A61N 5/06 |
| WO | 03/049633 A1 | 6/2003 | A45D 26/00 |
| WO | 2004/010884 A1 | 2/2004 | A61B 18/20 |
| WO | 2004/075731 A2 | 9/2004 | A61B 18/20 |
| WO | 2004/080279 A2 | 9/2004 | A61B 18/20 |
| WO | 2005/063193 A1 | 7/2005 | A61K 8/06 |
| WO | 2009/089177 A1 | 7/2009 | A61N 1/00 |

(56) References Cited

OTHER PUBLICATIONS

European Office Action, European application No. 04 712 910.1, 6 pages, Nov. 16, 2010.
Supplemental European Search Report, European application No. 04 712 922.6, 3 pages, Jul. 12, 2010.
Supplemental European Search Report, European application No. 04 712 911.9, 3 pages, Jun. 12, 2010.
Brunsting, L, et al., "The Color of the skin as Analyzed by Spectrophotometric Methods, II. The Role of Pigmentation", Section on Dermatology and Syphilology and the Division of Physics and Biophysical Research, The Mayo Foundation; pp. 575-592, Apr. 29, 1929.
Brunsting, L, et al., The Color of the Skin as Analyzed by Spectrophotometric Methods, III. The Role of Superficial Blook, Section on Dermatology and Syphilology and the Division of Physics and Biophysical Research, The Mayo Foundation; pp. 593-613, Apr. 29, 1929.
Angelopoulou, E., "The Reflectance Spectrum of Human Skin", Dept. of Computer & Information Science, Technical Reports (CIS), University of Pennsylvania; 14 pages, Dec. 2099.
U.S. Appl. No. 60/451,091, by Robert E. Grove, entitled "Method and Device for Handheld and Cordless Light-Based Epilation", Feb. 28, 2003.
U.S. Appl. No. 60/456,379, by Robert E. Grove, entitled "Apparatus and Method for the Radiative Treatment of Skin with Increased Eye Safety", Mar. 20, 2003.
U.S. Appl. No. 60/458,861, by Robert E. Grove, entilted "Method and Apparatus for Dermatologic Treatment Utilizing Battery-Powered Laser Diode Bars", Mar. 27, 2003.
U.S. Appl. No. 60/472,056, by Robert E. Grove, Entitled "Apparatus and Method for Dermatologic Treatment", May 20, 2003.
U.S. Appl. No. 60/450,243, by Robert E. Grove, entitled "Method and Apparatus for the Treatment of Benign Pigmented Lesions", Feb. 25, 2003.
U.S. Appl. No. 60/450,598, by Robert E. Grove, entitled "Personal Light Based Acne Treatment Device and Method", Feb. 26, 2003.
U.S. Appl. No. 60/452,304, by Robert E. Grove, entitled "Optical Sensor and Method for Identifying the Presence of Skin", Mar. 4, 2003.
U.S. Appl. No. 60/451,981, by Robert E. Grove, entitled "Method and Apparatus for the Repigmentation of Human Skin", Mar. 4, 2003.
U.S. Appl. No. 60/452,591, by Robert E. Grove, entitled "Method and Device for Sensing Skin Contact", Mar. 6, 2003.
U.S. Appl. No. 60/456,586, by Robert E. Grove, entitled "Handheld Dermatological Treatment Device with Power Meter", Mar. 21, 2003.
Extended European Search Report, Application No. 13159309.7, 7 pages, May 7, 2013.
Miller, Steve et al., "Isolation and Characterization of Protoporphyrin IX from Bacterial Catalase," The Journal of Biological Chemistry, vol. 235, No. 11, 3 pages, Mar. 7, 1960.
Brown, E.B., "Modern Optics," Radiometry and Photometry, Reinhold Publishing Corporation, 3 pages, 1965.
Cornelius, C.E. et al., "Red Fluorescence of Comedones: Production of Porphyrins by Corynebacterium Acnes," The Journal of Investigative Dermatology, vol. 49(4), PMID: 4228644, [PubMed—Indexed for Medline], 3 pages, Oct. 1967.
Dalton, J. et al., "Reaction Between Molecular Oxygen and Photoexcited Protoporphyrin IX," Nature, vol. 235, 1 pages, Feb. 18, 1972.
Hoeffler, Ulrich, "Enzymatic and Hemolytic Properties of Propionibacterium Acnes and Related Bacteria," Journal of Clinical Microbiology, vol. 6, No. 6, 4 pages, Jun. 10, 1977.
Formanek, I. et al., "Porphyrinsynthesis by Propionibacterium Acnes (author's translation)," Archives for Dermatological Research, vol. 259(2), German, PMID: 334087 [PubMed—indexed for Medline], 9 pages, Aug. 22, 1977.
Lee, W.L. et al., "Comparative Studies of Porphyrin Production in Propionibacterium Acnes and Propionibaceterium Granulosum," Journal of Bacteriology, vol. 133(2), PMID: 637914 [PubMed—Indexed for Medline] 5 pages, Aug. 25, 1977.
Mills, O.H. et al., "Ultraviolet Phototherapy and Photochemotherapy of Acne Vulgaris," Archives of Dermatological Research, , vol. 114(2), PMTD: 147054 [PubMed: Indexed for Medline] 3 pages, Feb. 1978.
Fanta, D. et al., "Porphyrinsynthesis of Propionibacterium Acnes in Acne and Seborrhea (author's translation)," Archives of Dermatological Research, vol. 261, German, PMID: 148872 [PubMed—indexed for Medline], 5 pages, Apr. 7, 1978.
McGinley, K.J. et al., "Facial Follicular Porphyrin Fluorescence: Correlation with Age and Density of Propionibacterium Acnes," British Journal of Dermatology, Vo. 102(4), PMID: 7387886 [PubMed—Indexed for Medline] 5 pages, Jul. 24, 1979.
Sliney, D. et al., "Safety with Lasers and Other Optical Sources, A Comprehensive Handbook," Plenum Press, 9 pages, Jul. 1980.
Fanta, D. et al., "Porphyrin Synthesis by Propionibacteria in Dependence of External Factors," Archives of Dermatological Research, vol. 271, 7 pages, Jul. 10, 1980.
Diffey, B. L. "The consistency of studies of ultraviolet erythema in normal human skin." Physics in medicine and biology 27.5, 6 pages, 1982.
Melo, T.B. et al., "In Vivo Porphyrin Fluorescence for Propionibacterium Acnes. A Characterization fo the Fluorescing Pigments," Dermatologica, vol. 164(3), PMID: 7084539 [PubMed—Indexed for Medline] 9 pages, Mar. 1982.
Parrish, J. et al., "Erythema and Melanogenesis Action Spectra of Normal Human Skin," Photochemistry and Photobiology, vol. 36, 5 pages, Mar. 15, 1982.
Kjeldstad, B. et al., "Influence of pH on Porphyrin Production in Propionibacterium Acnes," Archives of Dermatological Research, vol. 276(6), PMID: 6517611 [PubMed—Indexed for Medline] 5 pages, 1984.
Melo, T.B. et al., "Photodestruction of Propionibacterium Acnes Porphyrins," Z. Naturforsch, vol. 40(C), PMID: 3993179 [PubMed—Indexed for Medline] 4 pages, Oct. 22, 1984.
Kjeldstad, B. et al., "Porphyrin Photosensitization of Bacteria," Adv. Exp. Med. Biol., PMID: 4096295 [PubMed—indexed for Medline], 5 pages, 1985.
Kjeldstad, B. et al., "An Action Spectrum for Blue and Near Ultraviolet Inactivation of Propionibacterium Acnes; with Emphasis on a Possible Porphyrin Photosensitization," Photochemistry and Photobiology, vol. 43(1), PMID: 3952162 [PubMed—Indexed for Medline] 4 pages, Jul. 19, 1985.
Guideline for Limits of Exposure to Ultraviolet Radiation of Wavelengths between 180 nm and 400 nm, Health Physics, vol. 49, No. 2, 10 pages, Aug. 1985.
Meffert, H. et al., "Phototherapy of Acne Vulgaris with the "TuR" UV 10 Body Section Irradiation Unit [translation]," Dermatol. Monatsscher., vol. 172, German, PMID: 2938991 [PubMed—Indexed for Medline] 6 pages, 1986.
Meffert, H. et al., "Phototherapy of Acne Vulgaris with the UVA Irradiation Instrument TBG 400 [translation]," Dermatol. Monatsscher, vol. 172, German, PMID: 2937663 [PubMed—Indexed for Medline] 2 pages, 1986.
Johnsson, A. et al., "Fluorescence from Pilosebaceous Follicles," Archives of Dermatological Research, vol. 279(3), PMID: 3592747 [PubMed—Indexed for Medline] 4 pages, 1987.
Meffert, H. et al., "Treatment of Acne Vulgaris with Visible Light [translation]," Dermatol. Monatsscher, vol. 173, German, PMID: 2963772 [PubMed—Indexed for Medline] 2 pages, 1987.
Meffert, H. et al., "Verkuzung der Bestrahlungszeit Verwendung cines Hochruckstrahlers vom Blaulichttyp," Dermatol. Mon. schr 176, 8 pages, 1990.
Meffert, H. et al., "Therapy of Acne with Visible Light. Decreased Irradiation Time by Using a Blue-Light High-Energy Lamp [translation]" Dermatol. Monatsschr., German, PMID: 2150382 [PubMed—Indexed for Medline] 7 pages, 1990.
Kjeldstad, B. et al., "Near-UV-Induced Radicals in Propionibacterium Acnes, Studied by Electron Spin Resonance Spectrometry at 77 K.," Journal of Photochemistry and Photobiology, vol. 9(2), PMID: 1650821 [PubMed—Indexed for Medline] 7 pages, Sep. 21, 1990.

(56) References Cited

OTHER PUBLICATIONS

Morys et al., "The Accurate Measurements of Biologically Effective Ultraviolet Radiation," International Symposium on High Latitude Optics, 10 pages, Jul. 1993.
Webster, G.F., "Inflammation in Acne Vulgaris," Journal of the American Academy of Dermatology, vol. 33(2 Pt. 1), Review, PMID: 7622652 [PubMed—Indexed for Medline] 7 pages, Aug. 1995.
Leung, S., "The Porphyrin Page," website at http://www.washburn.edu-cas-chemistry-sleung-porphyrin/page.html, Created Apr. 16, 1996, Last Modified Nov. 11, 2002, printed Jun. 22, 2004, 7 pages, Apr. 16, 1996.
Arakane, K. et al., "Singlet Oxygen (1 delta g) Generation from Coproporphyrin in Propionibacterium Acnes on Irradiation," Biochemical and Biophysical Research Communication, vol. 223, Article No. 0937, PMID: 8687438 [PubMed—Indexed for Medline], 6 pages, Jun. 25, 1996.
Sigurdsson, V. et al., "Phototherapy of Acne Vulgaris with Visible Light," Dermatology, vol. 194(3), PMID: 9187844 [PubMed—Indexed for Medline] 5 pages, Nov. 15, 1996.
Predicate Devices: LightSheer Diode Laser System by Star Medical/Coherent Star, K973324, K982940, K001746, 1997.
Leyden, J., "Therapy for Acne Vulgaris," The New England Journal of Medicine, vol. 336, No. 16, Massachussetts Medical Society, 7 pages, Apr. 17, 1997.
UV Index definition, Canadian Environmental Web page, See entire document, 3 pages, Jun. 1, 1998.
Karu, Tiina, "Primary and Secondary Mechanisms of Action of Visible to Near-IR Radiation on Cells," Journal of Photochemistry and Photobiology, vol. 49, 17 pages, Nov. 9, 1998.
Saiki, Hiroyasu et al., "Diffusion of Porphyrins and Quinones in Organic Solvents," Phys. Chem. Chem Phys., vol. 1, 4 pages, 1999.
Code of Federal Regulations, Class I Accessible Emmission Limits for Laser Radiation, Food and Drug Administration, HHS, 2 pages, Apr. 1, 1999.
Yoo, Yeong-Min et al., "Hemoglobin Toxicity in Experimental Bacterial Peritonitis Is Due to Production of Reactive Oxygen Species," Clinical and Diagnostic Laboratory Immunology, vol. 6, No. 6, 2 pages, Jul. 12, 1999.
IEC Technical Report 60825-8, "Safety of Laser Products—Guide for the Safe Use of Medical Laser Equipment," 6 pages, Nov. 1999.
Papageorgiou, P. et al., "Phototherapy with Blue (415 nm) and Red (660 nm) Light in the Treatment of Acne Vulgaris," British Journal of Dermatology, vol. 142(5), PMID: 10809858 [PubMed—indexed for Medline] 6 pages, Dec. 7, 1999.
Romiti, R. et al., "High-Performance Liquid Chromatography Analysis of Porphyrins in Propionibacterium Acnes," Archives of Dermatological Research, vol. 292(6), PMID: 10929774 [PubMed—Indexed for Medline] 3 pages, Jan. 7, 2000.
Bagdonas, Saulius et al., "Phototransformations of 5-Aminolevulinic Acid-Induced Protoporphyrin IX in Vitro: A Spectroscopic Study," Photochemistry and Photobiology, vol. 72(2), 7 pages, May 6, 2000.
Shalita, A. et al., "Acne Photoclearing (APC) Using a Novel, High-Intensity, Enhanced, Narrow-Band, Blue Light Source," Clinical Application Notes, vol. 9(1), ESC Medical Systems Ltd., PB558-0230, Rev. A, 4 pages, 2001.
International Standard IEC 60825.1, Safety of Laser Products—Part 1: Equipment Classification, Requirements and User's Guide, Editon 1.2, 121 pages, 2001.
Koval'skaya, N.E. et al., "The Efficiency of the Formation of Singlet Oxygen by a Sensitizer Based on Zinc Phthlocyanine," Journal of Applied Spectroscopy, vol. 68, No. 2, 4 pages, 2001.
Buchezyk, Darius P. et al., "High Efficiency of 5-Aminolevulinate-Photodynamic Treatment Using UVA Irradiation," Carcinogenesis, vol. 22, No. 6, 5 pages, 2001.
Mason, Maria G. et al., "Extracellular Heme Peroxidases in Actinomycetes: a Case of Mistaken Identity," Applied and Environmental Microbiology, vol. 67, No. 10, 8 pages, Jul. 18, 2001.
Jappe, U. et al., "Propionibacterium Acnes and Inflammation in Acne; P. Acnes has T-Cell Mitogenic Activity," British Journal of Dermatology, vol. 146, 8 pages, Sep. 12, 2001.
Kawada, A. et al., "Acne Phototherapy with a High-Intensity, Enhanced, Narrow-Band, Blue Light Source: An Open Study and In Vitro Investigation," Journal of Dermatological Science, vol. 30(2), PMID: 12413768 [PubMed—indexed for Medline] 7 pages, Jun. 19, 2002.
Ashkenazi, H. et al., "Eradication of Propionibacterium Acnes by its Endogenic Porphyrins after Illumination with High Intensity Blue Light," FEMS Immunology and Medical Microbiology, vol. 35(1), PMID: 12589953 [PubMed: Indexed for MedLine], 8 pages, Jul. 24, 2002.
Harnessing Light to Treat Stretch Marks and Other Hypopigmented Scars, Skin & Aging, Supplement to Nov. 2002 Skin & Aging, Nov. 2002.
Elman et al., "The Effective Treatment of Acne Vulgaris by a High-Intensity, Narrow Band 405-420 nm Light Source," Journal of Cosmetic & Laser Therapy, vol. 5, 6 pages, Nov. 27, 2002.
Hode, L., "Are Lasers More Dangerous than IPL Instruments?," Lasers in Surgery and Medicine, Supplement 15, 3 pages, 2003.
Wagener, Frank et al., "Different Faces of the Heme-Heme Oxygenase System in Inflammation," Pharmaceutical Reviews, vol. 55, No. 3, The American Society for Pharmacology and Experimental Therapeutics, 21 pages, 2003.
Anonymous, "Akne-Guidelines Schweiz," [Online], Martin Pletscher: Dermatologie, Retrieved from Internet: http://www.martinpletscher.ch/dermatologie/akne.html, 5 pages, May 15, 2003.
Burkhart, Craig N. et al., "Assessment of Etiologic Agents in Acne Pathogenesis," Review, Department of Microbiology and Immunology, and Dermatology, Medical College of Ohio at Toledo, 7 pages, Jul. 2003.
Micro Touch Trimmer website, www.asseenontvwork.com/vcc/ideavillage/microtouch/104917, printed Dec. 4, 2003, 21 pages, Dec. 4, 2003.
Charakida, A. et al., "Phototherapy in the Treatment of Acne Vulgaris," American Journal of Clinical Dermatology, vol. 5(4), Adis. Data Information, 6 pages, 2004.
Elman, M. et al., "Light Therapy in the Treatment of Acne Vulgaris," Dermatological Surgery, vol. 30(2), Dermatology and Lasers Clinic, Tel Aviv and Caesarea, Israel, American Society for Dermatology Surgery, 8 pages, Feb. 2004.
U.S. Appl. No. 10/794,676, by Mark V. Weckworth et al. entitled "Method and Apparatus for the Repigmentation of Human Skin", Mar. 3, 2004.
Elman, M. et al., "The Role of Pulsed Light and Hear Energy (LHE) in Acne Clearance," Journal of Cosmetic Laser Therapy, vol. 6, 5 pages, Apr. 1, 2004.
Omi, Tokuya et al., "420 nm Intense Continuous Light Therapy for Acne," Journal of Cosmetic Laser Therapy, vol. 6, 7 pages, Aug. 12, 2004.
Krautheim, A. et al., "Acne: Topical Treatment," Clinics in Dermatology, vol. 22, No. 5, XP004647111, 10 pages, Sep. 1, 2004.
Ross, Victor E., "Optical Treatment for Acne," Dermatologic Therapy, vol. 18, ISSN 1396-0296, 14 pages, 2005.
Ross, Victor E., "Acne, Lasers, and Light," Advances in Dermatology, vol. 21, 29 pages, 2005.
Ortiz, Arisa et al., "A Review of Lasers and Light Sources in the Treatment of Acne Vulgaris," Journal of Cosmetic and Laser Therapy, vol. 7, 7 pages, Mar. 7, 2005.
Hamblin, M. et al., "*Helicobacter phylori* Accumulates Photoactive Porphyrins and Is Killed by Visible Light," Antimicrobial Agents and Chemotherapy, vol. 49, No. 7, American Society for Microbiology, 6 pages, Mar. 7, 2005.
Mariwalla, Kavita et al., "Use of Lasers and Light-Based Therapies for Treatment of Acne Vulgaris," Lasers in Surgery and Medicine, vol. 37, 10 pages, Oct. 12, 2005.
Mariwalla, Kavita et al., "Non-Traditional Acne Therapy: The Use of Lasers and Light-Based Therapies," US Dermatology Review 2006, 4 pages, 2006.
Tremblay, J.F. et al., "Light-Emitting Diode 415 nm in the Treatment of Inflammatory Acne: An Open-Label, Multicentric, Pilot Investigation," Journal of Cosmetic and Laser Therapy, vol. 8, 3 pages, Jan. 25, 2006.

(56) References Cited

OTHER PUBLICATIONS

Goldberg, David J. et al., "Combination Blue (415 nm) and red (633 nm) LED Phototherapy in the Treatment of Mild to Severe Acne Vulgaris, Jornal of Cosmetic and Laser Therapy," vol. 8, 5 pages, Mar. 29, 2006.
Lee, Seung Yoon et al., "Blue and Red Light Combination LED Phototherapy for Acne Vulgaris in Patients with Skin Phototype IV," Lasers in Surgery and Medicine, vol. 39, 9 pages, Nov. 16, 2006.
Nestor, M., "The Use of Photodynamic Therapy for Treatment of Acne Vulgaris," Dermatologic Clinics, vol. 25, 11 pages, 2007.
"Light Dose Ranging Study of Photodynamic Therapy (PDT) with Levulan + Blue Light in Severe Facial Acne," DUSA Pharmaceuticals, Inc., http://clinicaltrials.gov/ct2/show/NCT00706433, 25 pages, Mar. 2007.
Anonymous, "BlueLight Acne Treatments," [Online], Retrieved from Internet: http://www.topdocs.com/display_procedure.php?id=bluelight, 2 pages, Apr. 10, 2008.
"Comparison of Claro to Other Dermatological Devices for Acne Treatment," Quantitative Assessment of Light Illumination on Organism Reduction; Subculture agar: TSA + 5% Sheep's Blood (Blood agar) Organism Diluent: Butterfield's Buffer or 0.85% Saline; Propionibacterium Acnes (ATCC 11827), 16 pages, Jun. 23, 2008.
Anonymous, "Vi Derm Product Line," [Online], Kalil Medical Products, Retrieved from Internet: http://www.kalilmedical.com/doctor/vi_derm_products.asp, 4 pages, Mar. 2, 2010.
International Search Report, Application No. PCT/US2009/056961, 7 pages, Jun. 29, 2010.
International Preliminary Report on Patentability, PCT/US2009/056961, 11 pages, Mar. 22, 2011.
International Preliminary Report on Patentability, PCT/US2009/057204, 8 pages, Mar. 22, 2011.
Supplementary European Search Report, Application No. 09815144, 9 pages, Feb. 10, 2012.
European Office Action, Application No. 09815144.2, 6 pages, Oct. 10, 2012.
European Search Report, Application No. 08797565.2, 6 pages, Oct. 29, 2012.
Japanese Office Action, Application No. 2010-520342, 6 pages, Mar. 7, 2013.
European Office Action, Application No. 09815144.2, 5 pages, Apr. 3, 2013.
Japanese Office Action, Application No. 2009-261364, 7 pages, Jun. 18, 2013.
Shnitkind, E. et al., "Anti-Inflammatory Properties of Narrow Band Blue Light," Poster Presentation (Conference Unknown), 1 page.
Predicate Devices: SLP 1000 (LC 100) Diode Laser of Palomar Medical Technologies, K010580, K011747.
Predicate Devices: Apex 800 Pulsed Diode Laser of IRIDEX Corporation, K020849.
Predicate Devices: F1 Pulsed Diode Laser of Opus Medical, Inc., K030235.
Predicate Devices: LightSheer Diode Laser System manufactured by Lumenis, Ltd.
Predicate Devices: Quantum Flash Lamp System Manufactured by Lumenis, Ltd.
Predicate Devices: CoolGlide Excel YAG Laser by Altus, Inc.
Predicate Devices: Devices by Ya-Man Ltd., of Tokyo, Japan.
Predicate Devices: Oriel Instruments Model 48010, by Spectra-Physics, Stratford, CT.
Predicate Devices: Panasonic part No. P-170SCW, or HHR300SCP Ni-MH Rechargables, Panasonic P-170SCRP NiCd, by Panasonic Matsushita Electric Corporation of America, Secaucus, NJ.
Predicate Devices: Laser Diode Bar Packages, Part No. ASM06C040W08010B80, Cutting Edge Optronics, of St. Charles, MO.
Predicate Devices: Part No. HX8-101 or FAN-101, or CP 0.8-31-06L, from Melcor.
Predicate Devices: PIC18LF452, manufactured by Microchip Technologies of Chandler, AZ.
Predicate Devices: Transistors IRL3716 (International Rectifier Corp., El Segundo, CA).
Palomar Super Long Pulse Diode Laser System, Clinical Data, Palomar Medical Technologies brochure.
Japanese Office Action, Applcation No. 2011-506499, 5 pages, Nov. 26, 2013.
Japanese Office Action, Application No. 2011-527040, 14 pages.

\* cited by examiner

OPTICAL SENSOR AND METHOD FOR IDENTIFYING THE PRESENCE OF SKIN

PRIORITY

This application claims the benefit of priority under 35 U.S.C. §119(e) to U.S. patent application Ser. No. 10/787,720, filed Feb. 25, 2004, and to provisional patent applications No. 60/450,243, filed Feb. 25, 2003; 60/450,598, filed Feb. 26, 2003; 60/451,091, filed Feb. 28, 2003; 60/452,304, filed Mar. 4, 2003; 60/451,981, filed Mar. 4, 2003; 60/452,591, filed Mar. 6, 2003; 60/456,379, filed Mar. 20, 2003; 60/456,586, filed Mar. 21, 2003; 60/458,861, filed Mar. 27, 2003; and 60/472,056, filed May 20, 2003.

FIELD OF THE INVENTION

This invention relates generally to dermatological diagnostic devices and to dermatological therapeutic devices, and more particularly to dermatological devices that use radiation to probe and treat skin.

BACKGROUND ART

Over the past 15 years, lasers and intense pulsed light systems have been used to treat a wide array of dermatological skin conditions. Examples of such systems are the CoolGlide system manufactured by Altus, Inc. for the treatment of unwanted hair, the Quantum system, manufactured by Lumenis, Inc. for photo rejuvenation, and the VBeam system manufactured by Candela, Inc. for the treatment of vascular lesions. The light emitted by each of these systems is very intense and poses a hazard to both the operator and patient. Undesired or unexpected emission from these systems can cause blindness, skin damage (when cooling mechanisms are not properly applied prior to emission), and damage to furniture, clothing, or other unintended targets. The sale of each of these systems is restricted by the United States Food and Drug Administration (FDA), and the safety of treatments performed by these machines relies on a well-trained operator to determine if conditions are satisfactory for emission. However, even in the hands of a well-trained operator, the safe use of these types of systems would be enhanced if emission from the system were inhibited unless skin was the target.

In the future, devices similar to the above products may be developed that are intended for use by untrained users and offered for sale directly to consumers. Not only will such products benefit from the integration of a sensor that can restrict emission to only those times in which the device output is targeted to skin, the incorporation of a sensor may prove critical to the safe use of such devices. Just as with the FDA restricted systems described above, hazards posed by inadvertent emission from these direct-sale to the consumer products include thermal damage to the eye that may cause blindness, ignition of upholstery or clothing, or in the case of devices that could treat acne with blue or near ultraviolet (U.V.) radiation, unwanted chemical damage to the eyes. Sensors that permit untrained operators to use radiation emitting devices safely on their skin may be the enabling technology for home-use self-treatment with laser and intense light dermatological devices.

However, products that are sold directly to consumers for in-home self treatment must be inexpensive, reliable, and small, and uncomplicated to use. Therefore, any diagnostic system incorporated into a device intended for the consumer market is also preferably inexpensive, reliable, and small, and simple.

It should be noted that devices that merely sense and require contact with a surface prior to emission do increase the safety of these types of systems. However, a mere contact sensor can be easily fooled by surfaces other than skin. Therefore, a system that uses a sensor that can discriminate between skin and other surfaces in conjunction with a contact sensor, would be much more reliable in detecting surfaces that are not skin.

CURRENT STATE OF THE ART

The current state of the art of light-based dermatological devices is well described by considering typical devices available on the market. Two devices for light-based epilation are the LightSheer diode laser system manufactured by Lumenis Ltd., and the SLP-1000 fiber-coupled diode laser by Palomar Medical Technologies, Inc. Lasers and intense pulsed light systems are also used for the treatment of benign pigmented lesions and for photo-rejuvenation. An intense pulsed light (IPL) system, the Quantum, which is a powerful flashlamp system, also manufactured by Lumenis Ltd, is commonly used for photo-rejuvenation. These systems can be characterized by their relatively high radiation output. Typically these systems deliver greater than 10 J/cm$^2$, in time periods from about 5 ms to 500 ms, with optical emission powers typically in the range from 500 W to 2000 W. These devices are generally hazardous and are not appropriate for use by untrained personnel and their sale is often restricted to physicians.

More recently, much lower power devices such as a hair removal device manufactured by Ya-Man Ltd. Of Tokyo, and lower power blue LED devices for the treatment of acne have become available but have questionable efficacy or require long treatment times for use. These devices are typically capable of no more than about 1 W of radiative emission and are much less hazardous than the equivalent physician models or pose virtually no hazard at all. While these lower power systems do not require any features or devices to ensure safe use by the consumer, the trade off is questionable efficacy.

A consumer based device that is more efficacious, however, would require higher output power levels, would be inherently hazardous, and would benefit greatly from devices that would ensure safe use. Higher power consumer models, in general, are not currently available on the market not only because of safety concerns, but also because a small, reliable, inexpensive, and self-contained device, that can be conveniently used and stored by the average consumer is not easily conceived.

It is common for systems currently marketed for professional use to have safety features that restrict the emission of the devices to only those times when certain procedures are followed or certain conditions exist. For example, the Light-Sheer system manufactured by Lumenis, Inc. and used for laser hair removal, requires the operator to press and hold a footswitch prior to pulling the handpiece trigger that causes laser emission. The E-2000 system manufactured by Palomar, Inc., also used for laser hair removal, has perhaps the most advanced safety system of all of these dermatological systems. The E-2000 system uses a thermistor located near the output aperture of the device to measure changes in the temperature of the output aperture that occur if the device is in contact with skin. Based on these measurements of the temperature, automatic firing is restricted to times when the device is in contact with skin. This temperature safety system is presumably described in U.S. Pat. No. 6,508,813.

Characteristics of skin other than its temperature and thermodynamic properties could be used to identify skin. For example, electrical resistivity, hardness, chemical makeup, or acoustic properties would distinguish skin from other materials. However, the inventors of the subject application have identified through experiments a property of skin believed to have characteristics that are fairly unique and easily measured—its optical properties, specifically, the amount of radiation that is remitted at various wavelengths. Optical remittance is used herein to mean the total amount of light returned by a surface whether by spectral reflection, diffuse reflection, or by surface or subsurface scattering. Therefore, the remittance of skin would depend at least upon its index of refraction, roughness, optical absorption coefficient and optical scattering coefficient. Since several components of skin (blood, water, sebum, melanin, etc.) have optical absorption coefficients and optical scattering coefficients that are wavelength dependent, one would expect that the fraction of light remitted by skin would also depend on wavelength. Thus, in accordance with the present invention, the spectral remittance of skin, which is to mean the optical remittance as a function of wavelength, can be used to discriminate skin from other materials.

The spectral remittance of skin has been known and studied for years. In scientific papers as long ago as 1929, Bursting et al. described using a spectrophotometer to measure the optical remittance of skin as a function of wavelength. (See, Bursting, L. A. et al., "The Color of the Skin as Analyzed by Spectrophotometric Methods: II. The Role of Pigmentation", The Journal of Clinical Investigation, 1929, vol. 7, pp 574-592; and Bursting, L. A. et al., "The Color of the Skin as Analyzed by Spectrophotometric Methods: III. The Role of Superficial Blood", The Journal of Clinical Investigation, 1929, vol. 7, pp 593-613.) These papers identified the role of pigmentation and blood. Interestingly, a plot of spectral remittance versus wavelength shows characteristic dips at about 400 nm and 570 nm due to blood, and addition dips at about 740 nm and 980 nm due to water (see for example, U.S. Pat. No. 4,423,736). Overall remittance increases with wavelength through the visible portion of the electromagnetic spectrum due to decreasing absorption of melanin. Research shows that the characteristic spectral remission of skin is largely population-independent. Thus, it is conceivable to create a skin detector that could work reliably for skin from persons with different skin color due to different ethnicities.

Much of the recent research on the spectral remittance of skin has been done with the goal of discriminating diseased tissue from unaffected tissue. Since the optical properties of diseased and non-diseased skin can be expected to be much more subtle than the differences between the optical properties of skin and other materials such as plastic, textiles, or air, the light sources and detection systems used for these apparatuses are big, complex, and expensive.

In U.S. Pat. No. 4,423,736, DeWitt, et al. describe a system that uses a broad-band light source, filters, bifurcated optical fibers and a computer controlled spectroradiometer to measure the spectral remittance of skin for the identification of erythema. In addition to being large, complicated and expensive, the method involves obtaining a "baseline" spectral remittance from the individual's skin that is being analyzed. Obtaining a personalized baseline for each user of a dermatological device is unpractical. The light source and spectroradiometer are bulky and unsuitable for use within a small inexpensive dermatological treatment device.

In U.S. Pat. No. 4,486,184, Comment, et al. describe a device to measure the diffuse reflection and specular reflection of skin. Specular reflection, meaning a reflection whose incident angle is equal to its angle of reflection, should not be confused with spectral reflectivity, meaning the wavelength dependent reflectivity of a material. Although the device that is described has a means for radiating the skin and detecting the reflectance, and it is believed that there is no disclosure of a means for measuring the reflectance as a function of wavelength. Measuring the spectral reflectance of skin is more involved and is typically performed using large spectrophotometers.

In U.S. Pat. No. 5,556,612 Anderson et al. describe a method for treating diseased skin, especially skin affected by psoriasis. The method includes a step in which a non-invasive optical diagnostic method involving measuring the reflectance properties of diseased skin is used to determine the amount of topical photo-protection to apply to skin prior to radiation therapy. The non-invasive optical diagnostic is described as a measurement of the diffuse reflectance of light from the skin at the wavelength of the radiation used for treatment. It is believed that method and the device described do not measure the spectral reflectance of the skin, are not used to differentiate skin from other materials and it is not used to inhibit the delivery of therapeutic radiation.

In U.S. Pat. No. 5,628,744, Coleman, et al. describe a dermatological treatment device that incorporates two beams of radiation—a probe beam and a treatment beam. The reflectance of the probe beam is used to discriminate diseased skin form non-diseased skin. The probe beam, however, is described as monochromatic. Measuring the spectral reflectance of skin is more involved and is typically performed using large spectrophotometers.

Again, in U.S. Pat. No. 6,208,749, Gutkowicz-Krusin et al. describe a method and device for discriminating diseased tissue from normal tissue. Although the spectral remittance of the skin is measured, the method and device rely on the imaging of the skin and rely on an algorithm that demarks the boundary between diseased and normal tissue. The detector (imager), and a processor capable of manipulating the image data are relatively complex and not appropriate for use within a handpiece of a dermatological treatment device.

Lastly, in U.S. Pat. No. 6,436,127, Anderson, et al. describe a method for discriminating diseased skin that uses two different optical diagnostics. However, a method or device suitable for discriminating skin from other materials that requires only one optical diagnostic that is simple, small, inexpensive, and reliable is not described.

In summary, the current state of the art for home-use radiative therapeutics is limited to lower power devices of questionable efficacy. Safety features are not a concern in current home-use treatment devices because of their low output levels. Safety features in higher-power treatment devices for use by physicians are basic or not present because of the assumption that use is limited to trained, skilled operators. The radiative diagnostics that do exist in current therapeutic devices rely on simple techniques that require less complicated devices, or rely on methods that do not perform multi-wavelength measurements. Otherwise, the current state diagnostics rely on more complicated, and expensive techniques that involve the use of large, expensive, and complex spectroradiometers and spectrophotometers not well suited for use in a device intended for use by untrained and unskilled persons for self-treatment.

Clearly, a small, simple, inexpensive, and reliable sensor capable of discriminating skin from other materials for use as a safety feature of a dermatological treatment device would be desirable and beneficial. Furthermore, a dermatological treatment device that is powerful enough to provide efficacious treatment, has the convenience of a device small enough to fit entirely within the hand of the user, and incorporates appropriate sensors to ensure safe use by untrained, unskilled persons for self-treatment, would be desirable.

SUMMARY OF THE INVENTION

In accordance with a first aspect of the present invention, a device and method are provided for sensing the presence of human skin by evaluating the spectral remittance of electromagnetic radiation from the surface in question. In a simple form, the apparatus uses three or more LED's, each emitting radiation at a unique wavelength. Each LED, in turn, is used to illuminate the surface in question and the remitted light is measured by a detector, such as a silicon photo transistor. The remitted intensity at each wavelength is then compared with the known spectral remittance that is characteristic of skin. This configuration is described in more detail in the detailed description section of the subject application.

In accordance with the present invention, many other configurations of the sensor are also contemplated. For example, a single light source that emits at more than one wavelength such as an incandescent bulb could be used in combination with multiple detectors, each detector being capable of measuring the intensity of the remitted light within a narrow spectral band. Yet another configuration would use a single, broad band emitter such as an incandescent bulb, and single, broad band detector such as a silicon photo detector, and an optical filter wheel positioned in front of either the source or detector. The filter wheel would contain three or more filters; each filter passing a different portion of the electromagnetic spectrum. In turn, each filter would be rotated into the optics path and the remittance for each wavelength measured.

Furthermore, in another embodiment of the present invention, a dermatological treatment device incorporates a skin sensor that controls emissions from the treatment device. A preferred embodiment of such a device is battery powered, self-contained, and cordless. Such a device can incorporate one or more laser diode bars, for the treatment of unwanted hair. Another variation of such a device uses one or more blue LED's to emit an intense blue light for the treatment of acne. Each of the devices ensures safe use by inhibiting the emission of radiation unless skin is detected at the output aperture of the device. The device may also include a contact sensor that prevents emission of radiation unless there is also contact between the output aperture and a sufficiently firm surface such as skin.

It is therefore an object of the present invention to provide a method and apparatus for sensing the presence of human skin by evaluating remitted radiation from a surface in question against a known spectral remittance that is characteristic of skin.

It is another object of the present invention to provide a small, simple, inexpensive, and reliable sensor capable of discriminating skin from other materials for use as a safety feature in dermatological treatment devices.

It is a further object of the present invention to provide dermatological devices which are powerful enough to provide efficacious treatment, yet small enough to fit entirely within the hand of a user, and which incorporate a skin sensor to permit safe use by untrained, unskilled persons in a self-treatment environment.

It is still another object of the present invention to provide a skin sensor which employs a light source that provides light in three or more wavelength bands onto a surface being queried, a detector responsive to light remitted in the three or more wavelength bands from the surface being queried, and a circuit coupled to the detector which measures a spectral remittance of the surface being queried, and compares the spectral remittance against a reference spectral remittance for skin.

It is a still further object of the present invention to provide a dermatological treatment device which is self-contained, hand-held, and battery powered, and which has a skin sensor that inhibits the emission of treatment radiation from the treatment device unless the presence of skin is detected.

These and other objectives, features, and advantages of the present invention will become more readily apparent upon consideration of the following detailed description of certain preferred embodiments of the present invention and accompanying drawings.

INCORPORATION BY REFERENCE

What follows is a list of citations corresponding to references which are, in addition to those references cited above and below, and including that which is described as background and the invention summary, hereby incorporated by reference into the detailed description of the preferred embodiments below, as disclosing alternative embodiments of elements or features of the preferred embodiments that may not otherwise be set forth in detail below. A single one or a combination of two or more of these references may be consulted to obtain a variation of the elements or features of preferred embodiments described in the detailed description below. Further patent, patent application and non-patent references are cited in the written description and are also incorporated by reference into the preferred embodiment with the same effect as just described with respect to the following references:

U.S. Pat. Nos. 4,423,736; 4,846,184; 5,556,612; 5,628,744; 5; 6,208,749; 6,436,127; 6,508,813; and United States published application No. 2003/0036751; and U.S. provisional patent application No. 60/451,091, filed Feb. 28, 2003; 60/456,379, filed Mar. 20, 2003; 60/458,861, filed Mar. 27, 2003; 60/472,056, filed May 20, 2003; 60/450,243, filed Feb. 25, 2003; 60/450,598, filed Feb. 26, 2003; 60/452,304, filed Mar. 4, 2003; 60/451,981, filed Mar. 4, 2003; 60/452,591, filed Mar. 6, 2003; and 60/456,586, filed Mar. 21, 2003, all of which are assigned to the assignee of the subject application;

U.S. non-provisional patent application Ser. No. 10/787,720, entitled Optical Sensor and Method for Identifying the Presence of Skin, filed Feb. 25, 2004; U.S. patent application Ser. No. 11/829,747, filed Jul. 27, 2007, which is a divisional of U.S. non-provisional patent application Ser. No. 10/783, 880, filed Feb. 19, 2004, now U.S. Pat. No. 7,250,045, entitled "Self-Contained Eye-Safe Hair-Regrowth-Inhibition Apparatus And Method," naming as inventors Tobin C. Island, Robert E. Grove, and Mark V. Weckwerth; Ser. No. 10/783, 603, filed Feb. 19, 2004, entitled "Eye-Safe Dermatologic Treatment Apparatus And Method," naming inventors: Robert E. Grove, Mark V. Weckwerth, Tobin C. Island; and U.S. patent application Ser. No. 11/545,963, filed Oct. 10, 2006, which is a continuation of U.S. patent application Ser. No. 10/783,607, filed Feb. 19, 2004, now U.S. Pat. No. 7,118,563, entitled "Self-Contained, Diode-Laser-Based Dermatologic Treatment Apparatus And Method," naming as inventors: Mark V. Weckwerth, Tobin C. Island, Robert E. Grove, all of which are assigned to the assignee of the subject application (collectively "the Cross-Referenced Non-Provisional Applications"), all of which are incorporated herein by reference;

Angelopoulou et al., "The Reflectance Spectrum of Human Skin", Technical Report, Department of Computer and Information Science, 1999;

Bursting, L. A. et al., "The Color of the Skin as Analyzed by Spectrophotometric Methods: II. The Role of Pigmentation", The Journal of Clinical Investigation, 1929, vol. 7, pp 574-592; and Bursting, L. A. et al., "The Color of the Skin as Analyzed by Spectrophotometric Methods: III. The Role of Superficial Blood", The Journal of Clinical Investigation, 1929, vol. 7, pp 593-613.

DETAILED DESCRIPTION OF THE PREFERRED EMBODIMENTS

Figure 1:
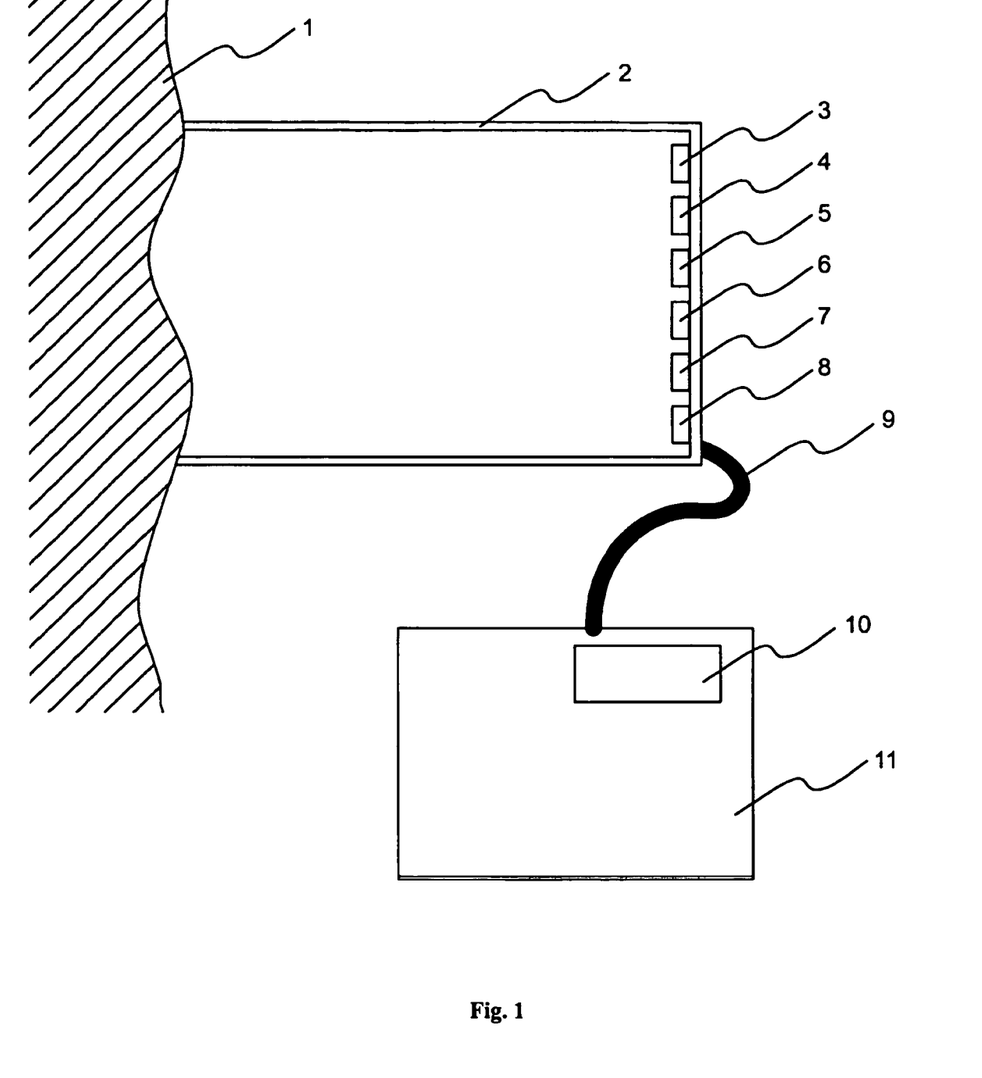
FIG. 1 is a simplified illustration of a sensor in accordance with the present invention.
Figure 2:
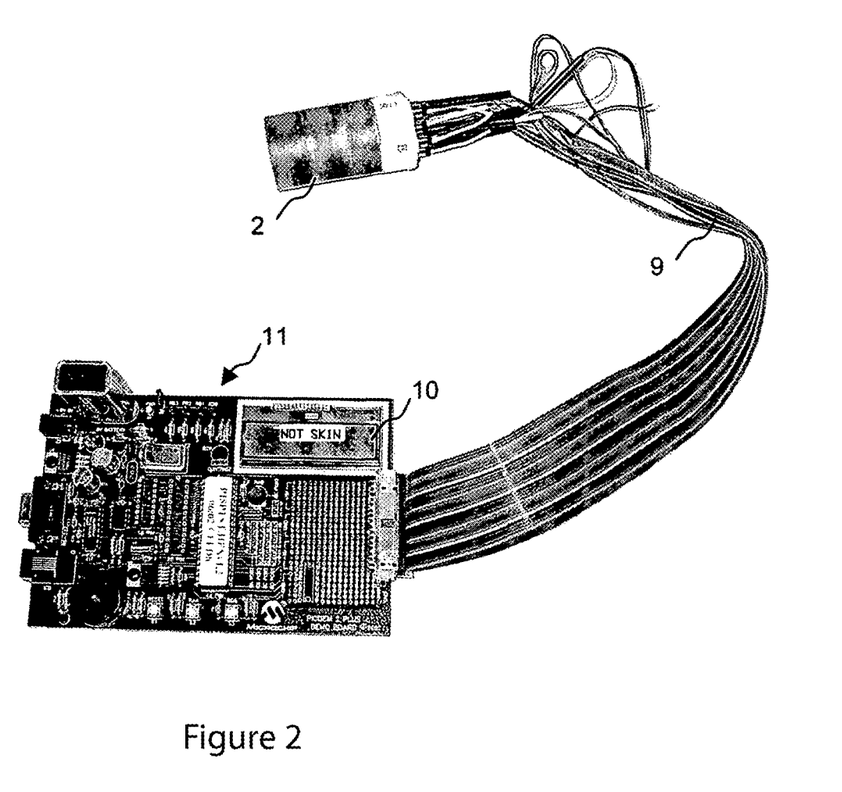
FIG. 2 is a photograph of a sensor including control circuitry in accordance with one embodiment of the present invention.

A detailed description of a configuration of the invention that uses multiple LED's as a light source and a single detector will now be described. FIG. 1 shows a drawing of such a sensor. While five (5) LED's are shown in FIG. 1, a smaller or greater number of LED's or other light sources can be used in this embodiment within the spirit of the present invention. FIG. 2 shows a photograph of the sensor, including control electronics.

The sensor of this embodiment has a chamber 2 that contains light sources 3, 4, 6, 7, and 8 and detector 5. Chamber 2 is open on the end opposite to the light sources 3, 4, 6, 7, and 8 and detector 5. Chamber 2 is made of an optically opaque material to prevent saturation of detector 5 by ambient lighting. In another embodiment of the current invention, light sources 3, 4, 6, 7, and 8 could be modulated so that frequency detection techniques can be used to resolve a relatively small signal from detector 5 even in the presence of strong ambient lighting. In such an embodiment, chamber 2 would not need to be opaque or chamber 2 could be eliminated.

Figure 3:
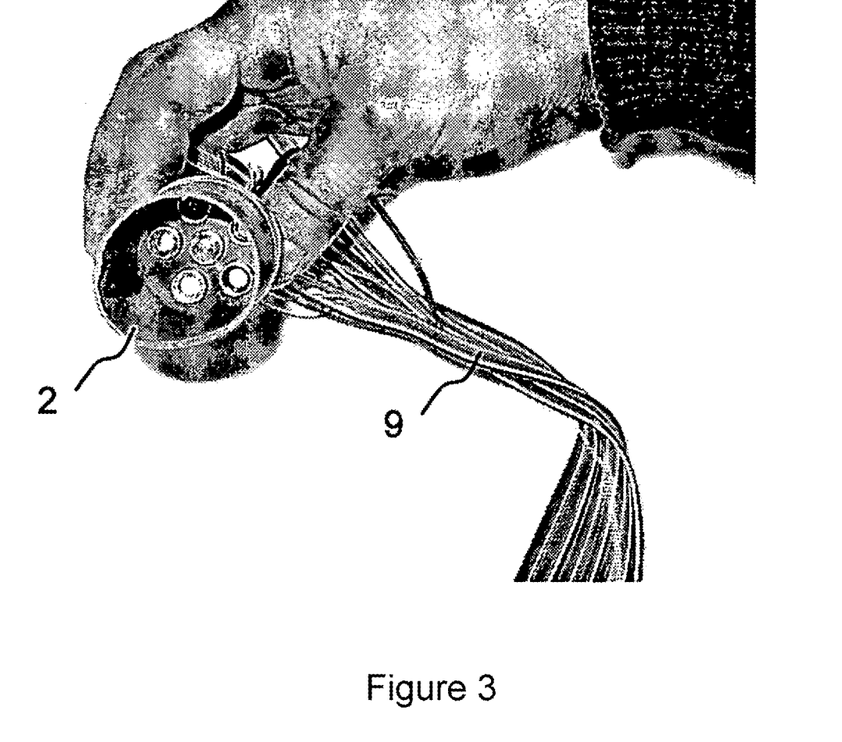
FIG. 3 is a photograph of the sensor of FIG. 2, looking into the chamber.

As shown in FIG. 2, the chamber can be made of a 1.5 inch diameter cardboard tube 2.75 inches in length. The closed end of the chamber is made by securing, such as by taping, an opaque disk of blue plastic over the end of the tube. A photograph looking into chamber 2 is shown in FIG. 3.

Light sources 3, 4, 6, 7, and 8 and detector 5 are mounted into holes drilled through the blue plastic disk. Light source 3 can be an infra-red LED with a typical peak emission at 940 nm (Radio Shack of Fort Worth, Tex., part #276-143). Light source 4 can be a red LED with a typical peak emission at 660 nm (Radio Shack part #276-309). Light source 6 can be a yellow LED with a typical peak emission at 587 nm (Radio Shack part #276-351). Light source 7 can be a green LED with a typical peak emission at 565 nm (Radio Shack part #276-304). Light source 8 can be a blue LED with a typical peak emission at 468 nm (Radio Shack part #276-316). Detector 5 can be a silicon npn photo transistor (Radio Shack part #276-145). Alternatively, the light source and detector could be located remotely to the chamber and the light could be transported to and from the chamber through fiber optics or light pipes.

Figure 4:
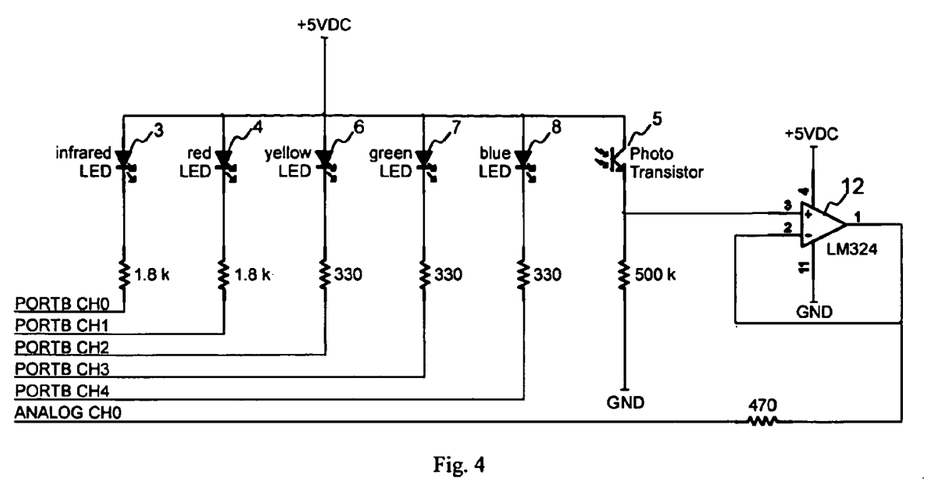
FIG. 4 is a simplified schematic diagram of a configuration of light sources and detector in accordance with an embodiment of the present invention.

Cable 9 is used to connect chamber 2, light sources 3, 4, 6, 7, and 8, and detector 5 to a microprocessor board 11. In the embodiment shown in FIGS. 3 and 4, microprocessor board 11 is a PICDEM 2 Plus Demo Board manufactured by Microchip, Inc. of Chandler, Ariz. The board was modified so that output pins on PORTB of the processor could turn on each light source 3, 4, 6, 7, and 8 individually. The board was also modified so that the output signal from detector 5 could be read by the analog input channel 0 of the processor. The board has a display 10 on which an indication of "SKIN" or "NOT SKIN" is made. Also included is an amplifier which is connected to receive the output of the detector 5, and to drive the analog input channel 0. The amplifier can be a LM324 operational amplifier, manufactured by National Semiconductor of Sunnyvale, Calif., connected as a voltage follower. A diagram of the electrical connections of the light sources 3, 4, 6, 7 and 8, the detector 5, the amplifier 12, and signal pins of the processor is given in FIG. 4.

In normal use, the open end of chamber 2 is placed against the surface to be measured, surface 1. The processor first measures the signal from detector 5 with all of the light sources 3, 4, 6, 7, and 8 off. This is the dark value and is used as a base-line for the signals of subsequent measurements. In turn, the processor turns on each of the light sources 3, 4, 5, 7, and 8, one-at-a-time, and measures the signal from detector 5 to arrive at an infra-red value, a red value, a yellow value, a green value, and blue value respectively. The measured dark value is subtracted from each of the measured radiation values to generate a set of adjusted values. "SKIN" is displayed on the display, indicating the presence of skin, if the following conditions are met for these adjusted values:

(infra-red value-dark value)>30
(infra-red value-dark value)<50
(green value-dark value)<10
(yellow value-dark value)<25
(red value-dark value)>40

Otherwise, "NOT SKIN", is displayed by the processor.

One skilled in the art will appreciate that the absolute numbers provided in the foregoing example are in arbitrary units, and that it is the relative relationship between these adjusted values that is of primary significance in the skin sensing method of the present invention.

The methodology described above is quite simple yet has proved to be very reliable in distinguishing human skin from a broad range of other surfaces such as cloth, metal, plastic, wood, etc. in experiments run by the inventors herein. Typical values obtained for various materials are given in Table 1. It has been found that a criterion for the remittance in the blue wavelength band was not needed to distinguish skin from common materials found in the office or home. Criteria for the blue remittance or a more complicated set of conditions for all of the color values can be developed that would provide even better discrimination between skin and other materials. However, a set of criteria that is too restrictive may not identify correctly some skin types since there is some variability in the optical properties of human skin. Conversely, if a lesser degree of discrimination is required for a certain application, then fewer light sources or a less restrictive set of criteria could be used. For any application, the complexity of the source and detector, the degree of discrimination desired, and tolerance of false negatives should be considered in determining the optimal design.

TABLE 1

|  | Caucasian skin | Asian skin | dark room | white paper | blue shirt | green paper | red plastic | wood | leather |
|---|---|---|---|---|---|---|---|---|---|
| dark | 0 | 2 | 1 | 0 | 0 | 0 | 0 | 0 | 0 |
| Infrared | 40 | 43 | 7 | 91 | 67 | 82 | 84 | 44 | 66 |
| red | 57 | 61 | 6 | 101 | 18 | 24 | 103 | 27 | 41 |
| yellow | 14 | 20 | 2 | 46 | 7 | 12 | 22 | 17 | 16 |
| green | 4 | 7 | 2 | 15 | 2 | 4 | 5 | 5 | 4 |
| blue | 13 | 19 | 3 | 60 | 17 | 15 | 8 | 16 | 9 |

The device just described could be miniaturized through the use of surface mountable LED's and detectors commonly found in packages as small as 0.06"×0.03" (SMT 0603 packages). The entire detector optical assembly could then be as small as 1 cm$^3$ or smaller. Through the use of surface mountable microcontrollers, resistors, and LED indicators, the electronics could be miniaturized to an equally small volume. Thus the device could be suitable for use as part of a small battery powered dermatological device.

Further, it is to be understood that in a commercial product, the devices, circuits and structures shown in FIGS. 1 through 4 can be incorporated into a more compact and integrated configuration, typically as a part of a treatment or therapeutic device. One such suitable configuration is described in the aforementioned Cross-Referenced Non-Provisional Applications, for example in U.S. Non-Provisional patent application, entitled "Self-Contained Eye-Safe Hair-Regrowth-Inhibition Apparatus And Method," incorporated by reference herein. In this cross-referenced application a self-contained, cordless, battery powered device is described. The device includes a housing which accommodates light sources, batteries, and electrical circuitry. In particular, FIG. 11 of the cross referenced application is a block diagram of the electronic circuitry for such device which can accommodate the specific light sources, amplifiers, and processing operations described herein. For example, in FIG. 11 of the cross-referenced application there is a skin sensor block 890 which communicates with a processor block 888 and with LED's 853, 854 and detectors 855, 856. One skilled in the art will readily appreciate that the processor block 888 can provide the processing operations performed by the processor of microprocessor board 11 described herein; and that skin sensor block 890 and LED's 853, 854 and detectors 855, 856 can correspond to the light sources 3, 4, 6, 7, and 8, and the detector 5, described herein.

In another embodiment of the sensor of the current invention a single broad-band radiation source such as an incandescent bulb is substituted for the multiple LED's. This embodiment employs multiple detectors, each sensitive to a distinct wavelength band. The control circuit measures the signal from each of the detectors. The detectors can be made sensitive to unique wavelength bands through the use of optical filters or by using detectors composed of materials inherently sensitive to different wavelength bands such as are gallium arsenide (GaAs), silicon (Si), and gallium nitride (GaN).

A Safe Therapeutic Dermatological Device Embodiment

Figure 5:
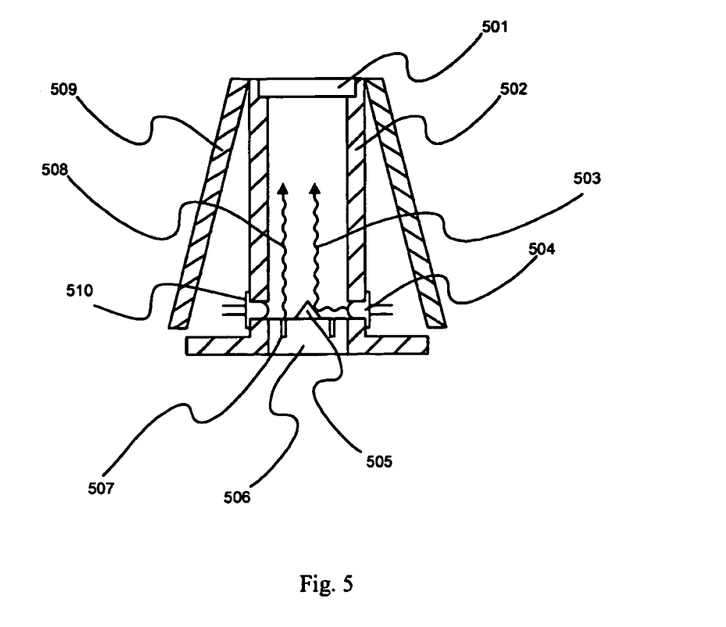
FIG. 5 illustrates the integration of an embodiment of a skin sensor into a therapeutic dermatological device in accordance with the present invention.

A drawing showing one configuration of the integration of the skin sensor into a therapeutic dermatological device is provided in FIG. 5. For clarity, only the head region near the output aperture is shown. As used in this example, the output aperture refers to the opening at the end of chamber 502 opposite radiation sources 507. Contained within housing 509 are two therapeutic radiation sources 507. A radiation source mount 506 is also shown. Radiation sources 507 may be laser diode bars that emit radiation suitable for the desired dermatological treatment. Radiation 508 is emitted from radiation source 507 into chamber 502 in the general direction of an output window 501 which is positioned in the output aperture. The skin sensor is comprised of one or more emitters 504 and one or more detectors 510 in accordance with the description of the skin sensor given previously. The emitter(s) 504 and detectors 510 can be oriented radially with respect to the light path in chamber 502. Emitted radiation 503 from the skin sensor emitters 504 takes generally a path as shown in the drawing. The emitted radiation 503 can be directed towards the same output aperture as is the therapeutic radiation 508 by a mirror 505. Thus, in the dermatologic treatment head embodiment of FIG. 5, the therapeutic radiation source 507 and the skin sensor emitters 504 and detector 510 share the same chamber 502 and the same output aperture. It is to be understood that the relative positions shown for emitter 504 and detector 510 in FIG. 5 are for illustration only, and that in practice other relative positions can be used. Also, not shown in FIG. 5 are other emitters 504 or detectors 510 positioned about the chamber 502. Further details about radiation sources 507, source mount 506, chamber 502, and output aperture 501, and therapeutic dermatologic devices in which they can be incorporated, can be found in the above mentioned Cross-Referenced Non-Provisional Applications.

Figure 6:
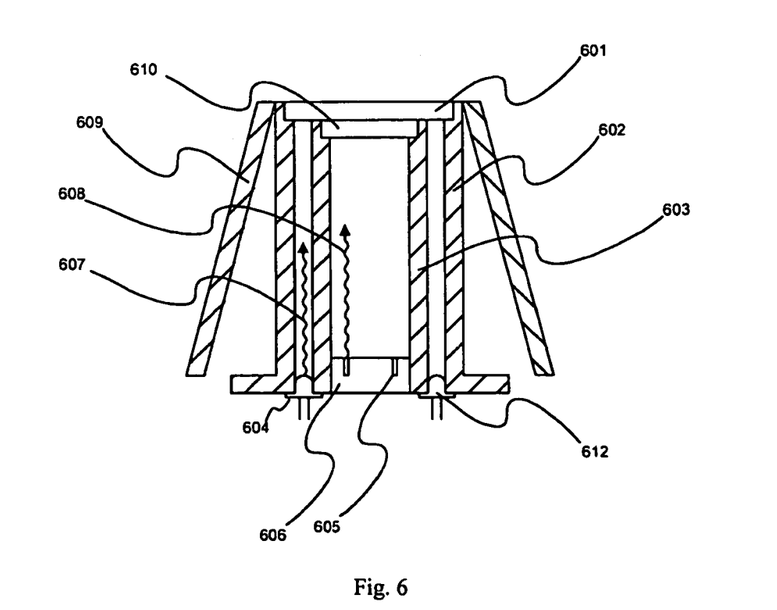
FIG. 6 illustrates an alternative integration and embodiment of the skin sensor in a therapeutic dermatological device in accordance with the present invention.

Another embodiment of a dermatological treatment head is shown in FIG. 6. This embodiment differs from the previous embodiment in that the therapeutic radiation source 605 and the skin sensor emitter 604 and detector 612 do not use the same aperture. Like the embodiment of FIG. 5, contained with housing 609 are two therapeutic radiation sources 605 mounted into source mount 606. The therapeutic radiation 608 is emitted into chamber 603 in the general direction of output window 601, and then through output window 601 which is positioned at the aperture at the end of chamber 603. In separate chamber(s) 602 along side the therapeutic treatment chamber 603 are located the emitter(s) 604 and detector(s) 612 of the skin sensor in accordance to the description of the skin sensor given previously. Emitters 604 are oriented axially with respect to a light path to the aperture. Radiation 607 from the skin sensor emitter 604 takes a path within chamber 602 as shown generally in the drawing. Thus, the skin sensor of this embodiment uses an annular-shaped aperture formed at the end of chamber 602, while the therapeutic radiation source 605 uses the aperture at the end of chamber 603. While an emitter 604 is shown on one side of the dermatological treatment head and detector 612 is shown on the other side thereof, it is to be understood that there may be other emitters 604 or detectors 612, not shown in FIG. 6, positioned adjacent to or spaced apart from the ones shown. In addition, other relative positions than the ones shown for emitter 604 and detector 612 may be used within the spirit of the present invention.

In the case of high power radiative therapeutic devices, it may be desirable to include a diffusing optical element 610 in the therapeutic beam that would reduce the eye hazard posed by the device. Diffuser 610 may also extend over the aperture of the skin sensor if desired without rendering the skin sensor inoperable. Further details about radiation sources 605, source mount 606, chamber 603, output aperture 601, diffuser 610, and therapeutic dermatologic devices in which they may be incorporated, may be found in the above mentioned Cross-Referenced Non-Provisional Applications.

Figure 7:
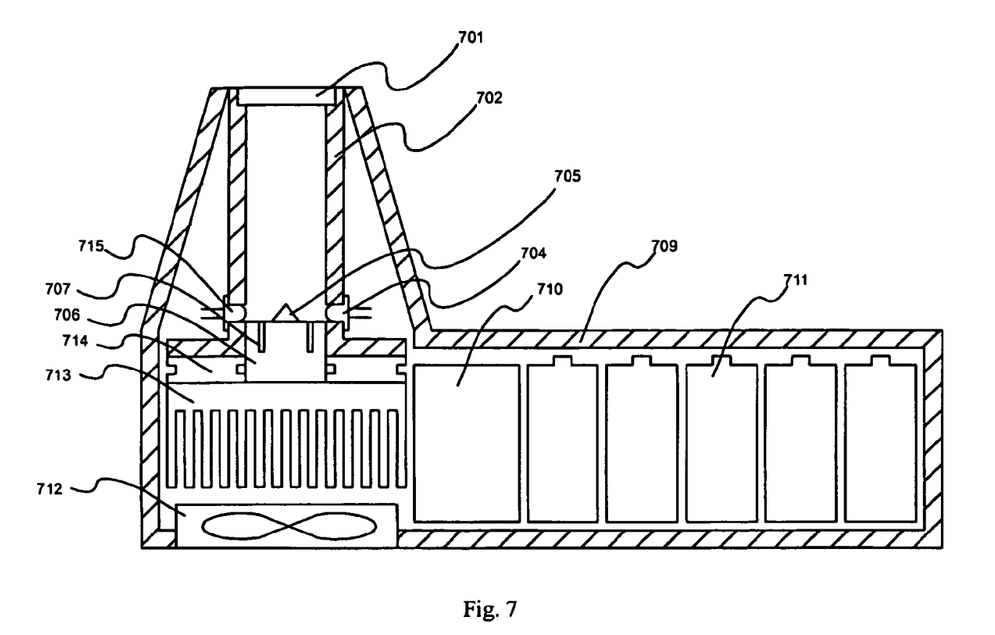
FIG. 7 illustrates a self-contained dermatological device incorporating the sensor embodiment of FIG. 5 in accordance with the present invention.

Referring now to FIG. 7, an example of a safe, small, yet powerful and efficacious dermatological device is shown which employs the therapeutic treatment head configuration of FIG. 5. Through innovative use of efficient radiation sources such as LED's or laser diodes, solid state thermoelectric coolers, innovative and efficient circuit design, and the integration of contact sensors and skin sensor, the device shown is entirely self-contained, small and light enough to fit within the grasp of a person's hand. One or more therapeutic radiation sources 707 are position within a mount 706. Therapeutic radiation source 707 is positioned such that radiation is emitted into chamber 702 and directed towards output window 701. Skin sensor radiation sources 704 and radiation detectors 715 are position to emit and collect radiation, respectively, from the aperture in housing 709. Output window 701 is kept cool by the conduction of heat through the walls of chamber 702, through thermoelectric (TE) cooling module 714, and finally into finned heat sink 713 which is cooled convectively by fan 712. Electronics 710 control emission of therapeutic radiation, the skin sensor and other devices within housing 709. Battery pack 711 provides power to the device. Reference is made to the above mentioned Cross-Referenced Non-Provisional Applications which provide further details about suitable dermatological devices of this type.

In other embodiments of the dermatological device of FIG. 7, other suitable radiation sources such as LED's or flashlamps are substituted for radiation sources 707. Also, some dermatological applications do not require the output window 701 to be thermally linked to the thermoelectric cooling modules 714. Still other embodiments of a suitable device would use a wired connection to another source of electrical power external to the handpiece portion of housing 709. In other embodiments, the finned heat exchanger 713 may be replaced by a thermal battery or other type of heat exchanger that may incorporate the use of water.

More specifically, the preferred embodiment of a laser hair removal device would be a self-contained, cordless device. It would use one or more laser diode bars to produce emission at about 808 nm. The exposure times of the skin would be about 400 ms, with the fluence of the exposure about 20 J/cm$^2$. The optical output power of the device preferably would be 60 W with a preferable treatment area of about 1 cm$^2$. The weight of the device would be about 750 g and the volume would be about 1000 cm$^3$. The safety features of the device would include a contact sensor and skin sensor. The device may also be made inherently less hazardous to a users' eyes through the use of a diffuser within the device that reduced the integrated radiance of the emission. Suitable diffusers are described in the Cross-Referenced Non-Provisional Applications.

A preferred embodiment of an acne treatment device in accordance with the present invention would be a self-contained, cordless device. It would use one or more LED's to produce emission at about 412 nm. The exposure times of the skin would be about 10 s, with the fluence of the exposure about 25 J/cm$^2$. The optical output power of the device would be about 2.5 W with a treatment area of about 1 cm$^2$. The weight of the device would be about 500 g and the volume would be about 500 cm$^3$. The safety features of the device would include a contact sensor and skin sensor. The device may also be made inherently less hazardous to the users' eyes through the use of a diffuser with the device that reduced the integrated radiance of the emission.

A preferred embodiment of a repigmentation device in accordance with the present invention would be a self contained, cordless device. It would use one or more LED's to produce emission in the wavelength range from 320 nm to 399 nm. The optimal power, and duration of the emission would depend strongly on the wavelength because of the higher effectiveness of shorter wavelengths. However, for a device producing radiation at 370 nm, 240 mW through an aperture 3 mm in diameter would generate about 33 J/cm$^2$ in about ten seconds. This dose would provide a significant fraction of a minimum erythemic dose (MED). The weight of the device would be about 500 g and the volume would be about 500 cm$^3$. The safety features of the device would include a contact sensor and skin sensor. The device may also be made inherently less hazardous to the users' eyes through the use of a diffuser within the device that reduced the integrated radiance of the emission.

While exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention, as set forth in the appended claims and structural and functional equivalents thereof.

In addition, in methods that may be performed according to preferred embodiments herein and that may have been described above, the operations have been described in selected typographical sequences. However, the sequences have been selected and so ordered for typographical convenience and are not intended to imply any particular order for performing the operations, unless expressly set forth in the claims or as understood by those skilled in the art as being necessary.

What is claimed:

1. A dermatological treatment device comprising:
an enclosed radiation chamber defined by:
a radiation chamber housing,
an output window at a first end of the radiation chamber housing and configured to be placed against a surface;
a radiation source mount located at a second end of the radiation chamber housing opposite the first end,
a source of treatment radiation supported by the radiation source mount at the second end of the radiation chamber and configured to emit treatment radiation though the enclosed radiation chamber and out through the output window, the treatment radiation configured to produce a fluence sufficient to provide a dermatological treatment; and
a sensor system comprising:
a sensor radiation source distinct from the source of treatment radiation and configured to emit radiation through the enclosed radiation chamber housing and toward the surface through the same output window, as the treatment radiation, and
a sensor detector configured to detect sensor radiation emitted by the sensor radiation source and remitted by the surface, wherein the sensor radiation source and the sensor detector are arranged in openings defined in the radiation chamber, and wherein the sensor system configured to:
measure radiation remitted via the surface; and
control delivery of treatment radiation to the surface based on the measured remitted radiation.

2. The dermatological treatment device of claim 1, wherein the source of treatment radiation is configured to produce a fluence through said treatment aperture sufficient to provide a dermatological treatment selected from the group consisting of: at least temporary inhibition of the regrowth of unwanted hair, treatment of acne, and repigmentation of skin.

3. The dermatological treatment device of claim 1, wherein:
the sensor system is configured to:
measure radiation remitted via the surface in multiple wavelength bands; and
control delivery of treatment radiation to the surface based on the measured remitted radiation in the multiple wavelength bands, including:
determining at least one spectral remittance of the surface based on the measured remitted radiation in the multiple wavelength bands; and
controlling delivery of treatment radiation to the surface based on the at least one determined spectral remittance.

4. The dermatological treatment device of claim 1, wherein:
the sensor system is configured to:
measure radiation remitted via the surface in multiple wavelength bands; and
control delivery of treatment radiation to the surface based on the measured remitted radiation in the multiple wavelength bands, including:
determining at least one spectral remittance of the surface based on the measured remitted radiation in the multiple wavelength bands;
comparing the at least one spectral remittance of the surface with at least one reference spectral remittance; and
controlling delivery of treatment radiation to the surface based on the results of the comparison.

5. The dermatological treatment device of claim 4, wherein:
determining at least one spectral remittance of the surface based on the measured remitted radiation in the multiple wavelength bands comprises determining a spectral remittance of the surface for each wavelength band based on the measured remitted radiation in that wavelength band; and
comparing the at least one spectral remittance of the surface with at least one reference spectral remittance comprises comparing the spectral remittance for each wavelength band with a reference spectral remittance corresponding to that wavelength band.

6. The dermatological treatment device of claim 4, wherein the at least one reference spectral remittance comprises at least one reference spectral remittance indicative of skin.

7. The dermatolotical treatment device of claim 1, wherein the sensor system is configured to:
determine, based on the measured remitted radiation in multiple wavelength bands, whether the surface is skin; and
control delivery of treatment radiation to the surface based on whether the surface is determined to be skin.

8. The dermatological treatment device of claim 1, wherein the sensor system comprises:
at least one broad-band radiation source; and
multiple detectors responsive to different wavelength bands.

9. The dermatological treatment device of claim 1, wherein the sensor system comprises:
the one or more radiation sources being configured to emit radiation in multiple different wavelength bands; and
multiple detectors responsive to different wavelength bands.

10. The dermatological treatment device of claim 1, wherein the sensor system is configured to emit radiation in multiple different wavelength simultaneously.

11. The dermatological treatment device of claim 1, wherein the sensor system is configured to emit radiation in multiple different wavelength bands is emitted at different times.

12. The dermatological treatment device of claim 1, wherein the sensor system is configured to emit radiation in multiple wavelength bands separated from each other.

13. The dermatological treatment device of claim 1, wherein the sensor system is configured to emit radiation in at least three different wavelength bands.

14. A dermatological treatment device comprising:
a source of treatment radiation and positioned to deliver radiation through a treatment radiation chamber and through a unitary outlet window configured to be placed against a surface; and
a sensor system for analyzing a surface for treatment by a dermatological treatment device, the sensor system comprising:
one or more emitters configured to emit radiation onto a surface;
one or more detectors configured to receive radiation remitted via the surface;
a processor configured to:
measure the received remitted radiation in at least one wavelength band;
determine at least one spectral remittance of the surface based on the measured remitted radiation in the at least one wavelength band;
compare the at least one spectral remittance of the surface with at least one reference spectral remittance; and
control the dermatological treatment device based on the measured remitted radiation,
wherein the one or more emitters of the sensor system are distinct from the source of treatment radiation and arranged to emit sensor system radiation through an annular sensor system chamber extending around the treatment radiation chamber and physically separated from the treatment radiation chamber by an annular wall, and
wherein the unitary outlet window extends over an outlet end of the annular sensor system chamber, such that the sensor system radiation is emitted through the same unitary outlet window as the treatment radiation.

15. The dermatological treatment device of claim 14, wherein:
determining at least one spectral remittance of the surface based on the measured remitted radiation in the at least one wavelength band comprises determining a spectral remittance of the surface for each wavelength band based on the measured remitted radiation in that wavelength band; and comparing the at least one spectral remittance of the surface with at least one reference spectral remittance comprises comparing the spectral remittance for each wavelength band with a reference spectral remittance corresponding to that wavelength band.

16. The dermatological treatment device of claim 14, wherein the at least one reference spectral remittance comprises at least one reference spectral remittance indicative of skin.

17. The dermatological treatment device of claim 14, wherein the sensor system is configured to:
    determine, based on the comparison of the at least one spectral remittance of the surface with the at least one reference spectral remittance, whether the surface is skin; and
    control the dermatological treatment device based on whether the surface is determined to be skin.

18. The dermatological treatment device of claim 14, wherein:
    the one or more emitters of the sensor system comprises at least one broad-band radiation source; and
    the one or more detectors of the sensor system comprises multiple detectors responsive to different wavelength bands.

19. The dermatological treatment device of claim 14, wherein the sensor system comprises:
    the one or more emitters of the sensor system are configured to emit radiation in multiple different wavelength bands; and
    the one or more detectors of the sensor system comprise multiple detectors responsive to the multiple different wavelength bands.

20. The dermatological treatment device of claim 14, wherein the sensor system is configured to emit radiation in at least three different wavelength bands.

* * * * *